US011076739B2

(12) United States Patent
Olschan et al.

(10) Patent No.: US 11,076,739 B2
(45) Date of Patent: Aug. 3, 2021

(54) BODILY FLUID CLEANUP SYSTEM

(71) Applicant: Acme United Corporation, Fairfield, CT (US)

(72) Inventors: Brian S. Olschan, Madison, CT (US); Jodi Farina, Fairfield, CT (US); David Schweitzer, Weston, CT (US)

(73) Assignee: Acme United Corporation, Fairfield, CT (US)

( * ) Notice: Subject to any disclaimer, the term of this patent is extended or adjusted under 35 U.S.C. 154(b) by 196 days.

(21) Appl. No.: 16/327,569

(22) PCT Filed: Mar. 27, 2018

(86) PCT No.: PCT/US2018/024553
§ 371 (c)(1),
(2) Date: Feb. 22, 2019

(87) PCT Pub. No.: WO2018/183317
PCT Pub. Date: Oct. 4, 2018

(65) Prior Publication Data
US 2019/0200834 A1 Jul. 4, 2019

Related U.S. Application Data

(60) Provisional application No. 62/477,464, filed on Mar. 28, 2017, provisional application No. 62/594,151, filed on Dec. 4, 2017.

(51) Int. Cl.
*A47L 13/52* (2006.01)
*A61B 50/36* (2016.01)
(Continued)

(52) U.S. Cl.
CPC ............ *A47L 13/52* (2013.01); *A46B 5/0095* (2013.01); *A61B 50/36* (2016.02); *B25G 1/04* (2013.01);
(Continued)

(58) Field of Classification Search
CPC ... A47L 13/52; A61B 50/36; E01H 2001/126; E01H 1/1206; B65D 5/6625; B65D 5/242; B09B 3/0075
(Continued)

(56) References Cited

U.S. PATENT DOCUMENTS 3,121,248 A * 2/1964 Ferguson ................. A47L 13/52
15/257.9
3,534,424 A * 10/1970 Levinson ............... E01H 1/1206
15/105
(Continued)

FOREIGN PATENT DOCUMENTS

CN 201284473 8/2009
GB 2242613 A * 10/1991 ........... E01H 1/1206
(Continued)

OTHER PUBLICATIONS

Computer generated English translation of CN 201284473 Y, Zhihong, published Aug. 2009. (Year: 2009).*
(Continued)

*Primary Examiner* — Laura C Guidotti
(74) *Attorney, Agent, or Firm* — Alix, Yale & Ristas, LLP

(57) ABSTRACT

A bodily fluid cleanup system is configured to be assembled, employed and subsequently disposed of to safely remove biohazardous material from an area. The system includes a disposable receptacle and a plurality of disposable modular components for assembling a plurality of disposable modular implements, all of which may be enclosed within a single package. The modular implements may include, but are not limited to, a wiper blade, a broom, a dustpan and/or a mop. The receptacle transitions between an open position and a closed position and in an embodiment includes a base, an integral cover, a molded bottom edge insert and a molded mounting member which all form an enclosure that func-
(Continued)

tions to house various materials and the implements in a pre-usage configuration and to retain biohazardous material during a cleanup process.

20 Claims, 29 Drawing Sheets

(51) Int. Cl.
| | | |
|---|---|---|
| *E01H 1/12* | (2006.01) | |
| *B25G 1/04* | (2006.01) | |
| *B25G 3/04* | (2006.01) | |
| *A46B 5/00* | (2006.01) | |
| *B08B 1/00* | (2006.01) | |
| *A46B 1/00* | (2006.01) | |
| *A47L 13/11* | (2006.01) | |
| *A47L 13/256* | (2006.01) | |
| *B25G 1/06* | (2006.01) | |
| *B25G 3/08* | (2006.01) | |
| *B25G 3/38* | (2006.01) | |
| *B09B 3/00* | (2006.01) | |

(52) U.S. Cl.
CPC .............. *B25G 3/04* (2013.01); *E01H 1/1206* (2013.01); *A46B 1/00* (2013.01); *A46B 2200/302* (2013.01); *A47L 13/11* (2013.01); *A47L 13/256* (2013.01); *B08B 1/00* (2013.01); *B09B 3/0075* (2013.01); *B25G 1/06* (2013.01); *B25G 3/08* (2013.01); *B25G 3/38* (2013.01)

(58) Field of Classification Search
USPC ........................ 15/257.1, 257.6, 257.7, 257.9
See application file for complete search history.

(56) References Cited

U.S. PATENT DOCUMENTS

| | | | |
|---|---|---|---|
| 3,685,088 A * | 8/1972 | Doherty | ................ E01H 1/1206 294/1.3 |
| 3,727,956 A | 4/1973 | Popeil | |
| 4,979,669 A * | 12/1990 | Kerton | ................. B65D 5/6626 229/144 |
| 2004/0134803 A1 | 7/2004 | Michelson et al. | |
| 2010/0065448 A1* | 3/2010 | Vargas | .................... A47L 13/52 206/223 |
| 2014/0150196 A1 | 6/2014 | Fascio et al. | |
| 2019/0210075 A1* | 7/2019 | Smith | ....................... B08B 3/10 |

FOREIGN PATENT DOCUMENTS

| | | | | |
|---|---|---|---|---|
| WO | WO 2007/053690 | * | 5/2007 | ............. A61B 50/36 |
| WO | WO2007053690 | | 5/2007 | |

OTHER PUBLICATIONS

International Preliminary Report on Patentability dated Jun. 8, 2018.
Search Report and Written Opinion dated Jun. 8, 2018.

* cited by examiner

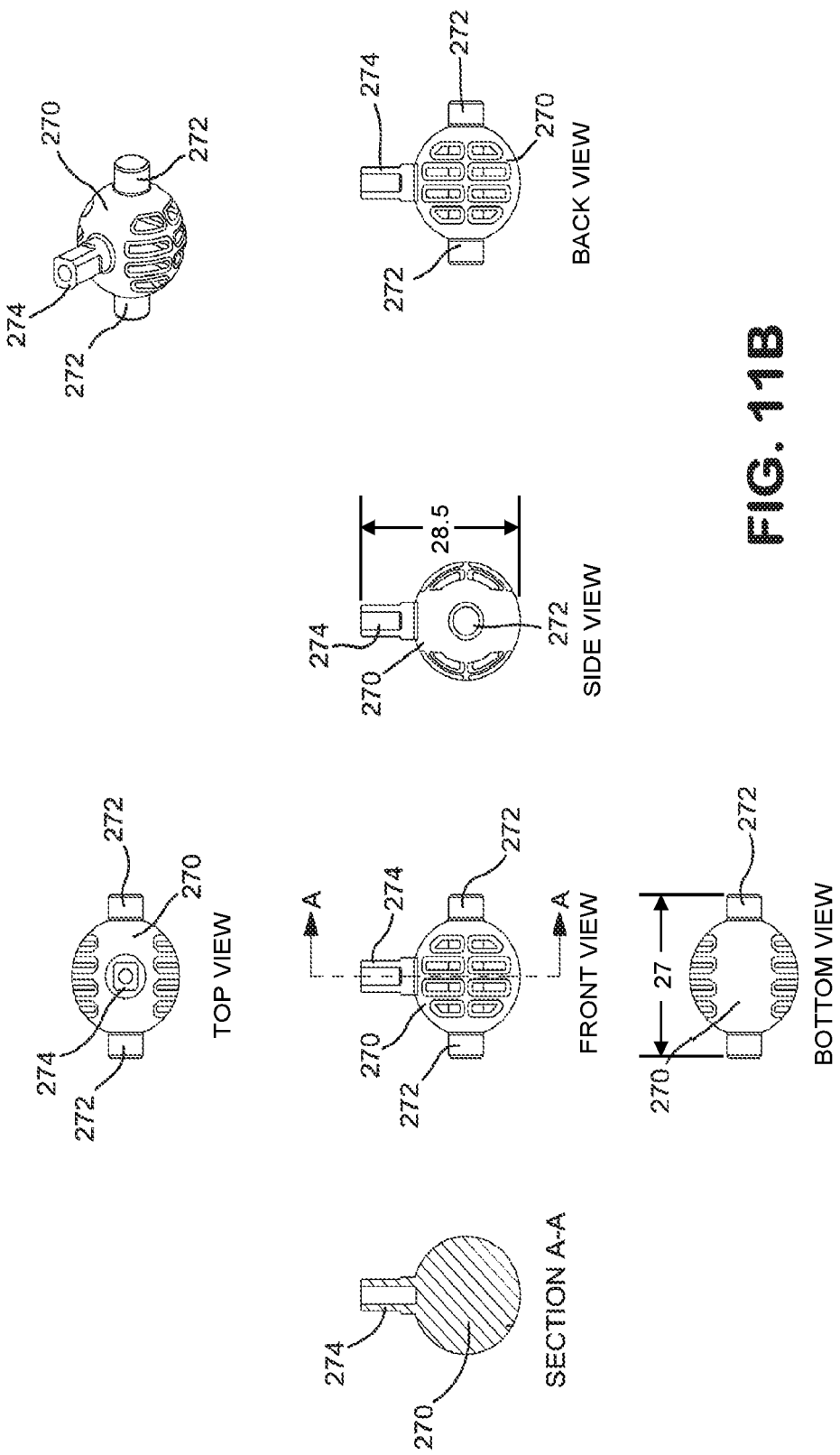

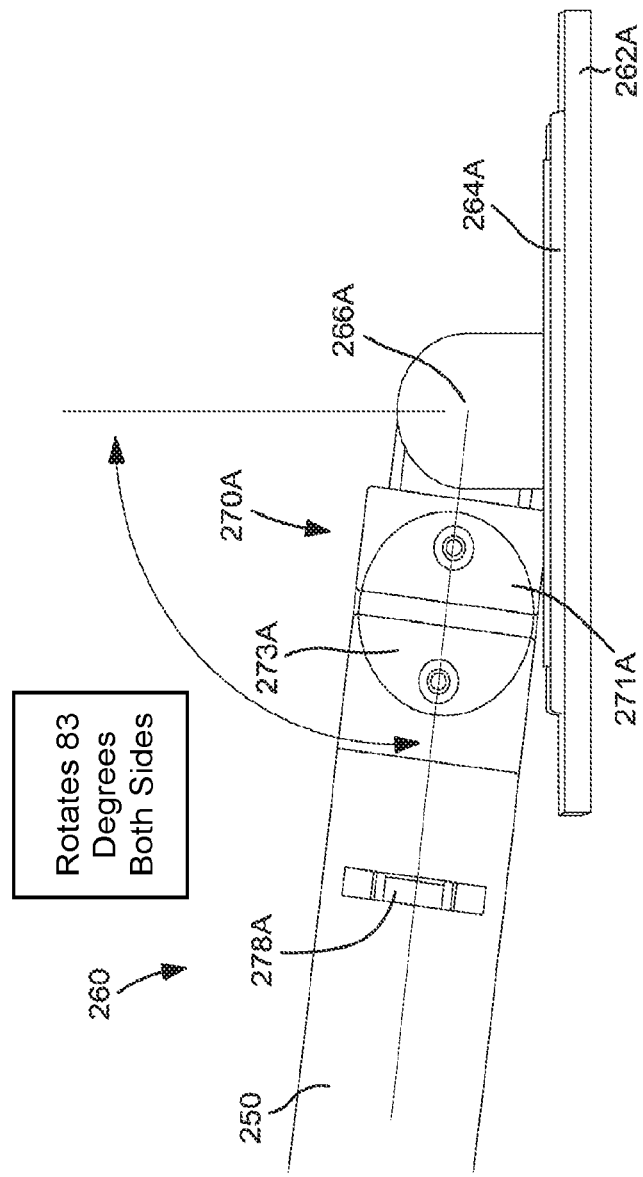

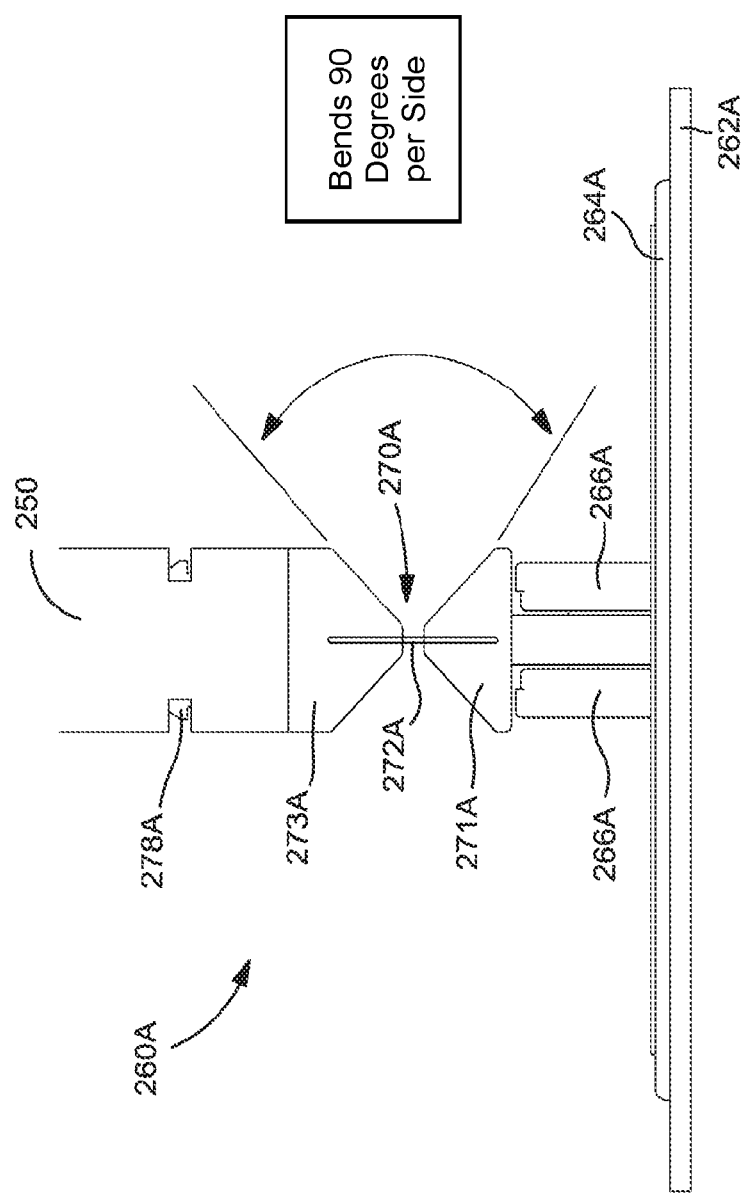

BODILY FLUID CLEANUP SYSTEM

BACKGROUND

This disclosure relates generally to devices, material and methods for cleaning up biohazardous materials. More particularly, this disclosure relates to methods and devices for cleaning up bodily fluids such as vomit, feces and urine.

Bodily fluid spills in public areas occur frequently and potentially present a significant health hazard. Numerous jurisdictional laws, regulations and guidelines, such as the Occupational Safety and Health Administration (OSHA) in the United States, at least partially set forth standards for cleaning up bodily fluids, including standards which address safety concerns to the employee and the workplace. There are also laws, regulations and requirements in the United States, as well as other nations, for disposing of both the spills and the protective material and devices used in connection with cleaning such spills.

In the United States, the Environmental Protection Agency (EPA) has regulations directed to cleaning chemicals and sanitizers and to the method and precautions for people using such material, as well as for the general public which may come in contact with such material. In the United States, bodily spills also present a potential for infection from noroviruses which may be regulated both indirectly and directly by OSHA, the Center for Disease Control (CDC), and EPA at the federal level. In addition, the procedures related to bodily spill cleanup can be subject directly or indirectly to jurisdictional regulations and agency guidelines detailing the requirements for bodily spill cleanup. Non-United States jurisdictions also have similar requirements for bodily spill cleanup in public facilities and areas.

The present disclosure addresses the need for efficient and safe cleanup of bodily spills. The disclosed bodily fluid cleanup system provides for both the worker and the general public in a manner that is compliant with relevant health and safety laws, regulations and guidelines.

SUMMARY

According to aspects illustrated herein, a bodily fluid cleanup system (hereafter, "the system") is configured to be assembled, employed and subsequently disposed of to safely remove biohazardous material from an area. The system includes a disposable receptacle and a plurality of disposable modular components for assembling a plurality of disposable modular implements, all of which are enclosed within a single package. The modular implements may include, but are not limited to, a wiper blade, a broom, a dustpan and/or a mop.

The receptacle is capable of transitioning between an open position and a closed position and includes a base, an integral cover, a molded bottom edge insert and a molded mounting member which all form an enclosure that functions to house various materials and tools in a pre-usage configuration and retain biohazardous material during a cleanup process.

The base of the receptacle includes a bottom, two opposed base sides, a rear and an open front having a front edge. The bottom edge insert is mounted to the bottom of the base and forwardly inclined to contact a floor area where the biohazardous material is present. The bottom edge insert also includes a rearward retainer lip to hold the biohazardous material within the receptacle and a pair of opposed projections for engaging the cover when the receptacle is in a closed position.

The cover is capable of pivoting to the rear of the base and includes a top, two opposed cover sides, two opposed retainer apertures for engaging the projections of the insert and gussets that connect the cover sides to the base sides. The gussets create an over-center configuration which provides a closing and locking force that urges the cover to close over the base. The mounting member is attached to the cover and is engageable with the front edge of the base. The mounting member also includes an integrally mounted hinged connector for coupling with a tube used to attach to a handle assembly.

In use, the modular components are unpacked from the receptacle and assembled to form the modular implements. The handle assembly is constructed and mounted to the receptacle. The biohazardous material is then moved and/or swept over the front edge of the base into the receptacle. The cover is closed over the base and locked by the projections extending through the apertures. The handle assembly is disassembled and dismounted from the receptacle. The other modular implements are also disassembled. The closed receptacle, modular components and any other materials are placed in a container which is then closed and placed in a proper and safe disposal.

BRIEF DESCRIPTION OF THE DRAWINGS

Aspects of an embodiment will be described in reference to the drawings, where like numerals reflect like elements:

FIG. 8C is an annotated fragmentary perspective view of the broom embodiment of FIG. 8 further illustrating a handle pivot portion thereof;

FIG. 9C is a perspective view of the broom of FIG. 9 illustrated in a tilted position;

FIG. 9D is a perspective view of the broom of FIG. 9 illustrating the broom in a straight configuration;

FIG. 11B is an annotated drawing, partly diagrammatic, illustrating various views of a ball joint for the mop of FIG. 11;

FIG. 12D is an annotated enlarged fragmentary side view, partly diagrammatic, of the mop of FIG. 12;

FIG. 12E is an annotated enlarged fragmentary frontal view, partly diagrammatic, of the mop of FIG. 12;

DETAILED DESCRIPTION

Figure 1:
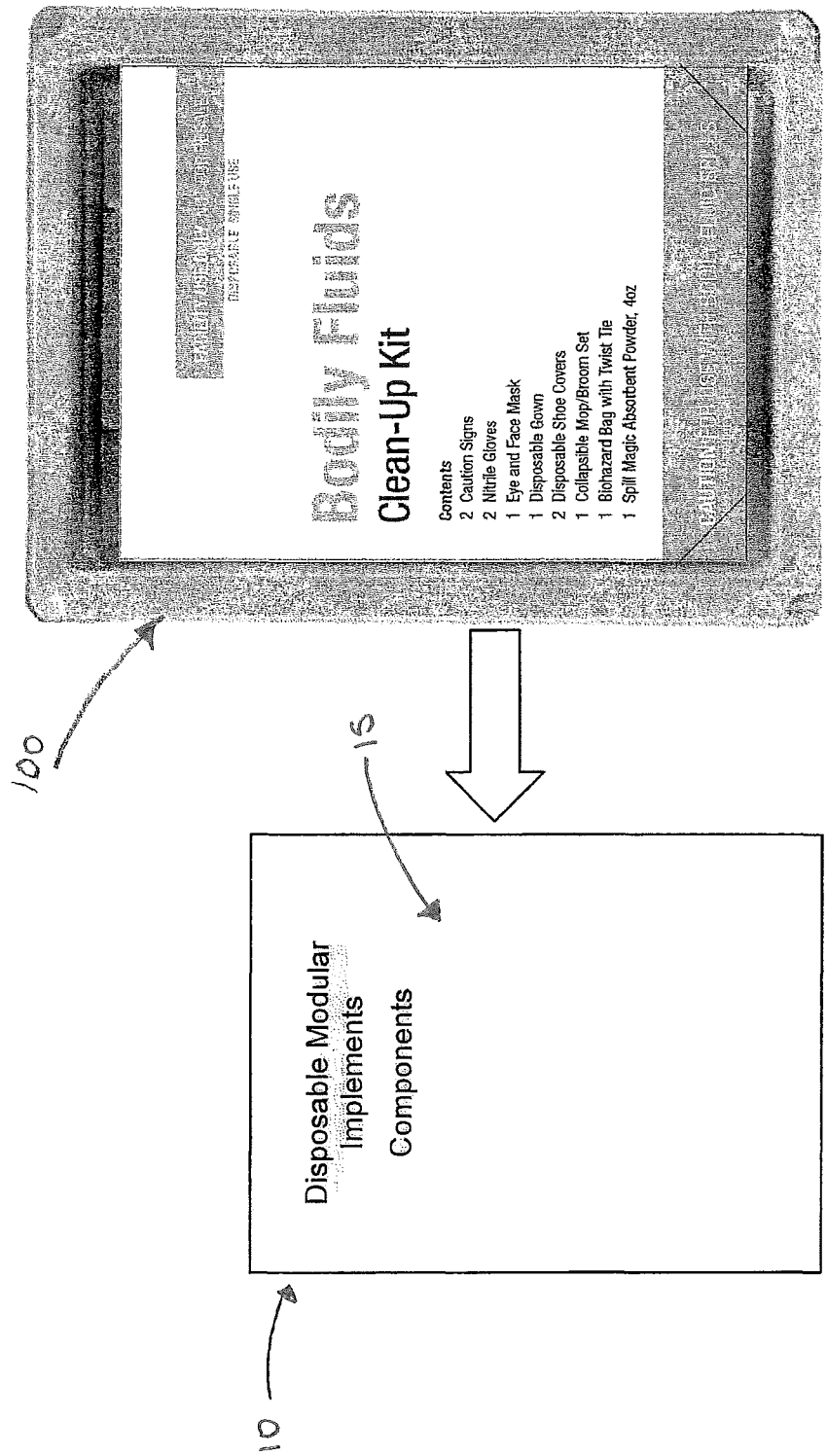
FIG. 1 is an annotated front view, partly schematic, of a bodily fluid cleanup system (hereafter, "the system")

An embodiment of a bodily fluid cleanup system (hereafter, "the system") employs a disposable receptacle 110 and disposable modular implements 15, all of which are preferably enclosed within a single package. Embodiments of the system will now be described with reference to FIGS. 1-18. The system will generally be referred to by the reference numeral 100. Various material, methods of construction, methods of manufacture, and methods of fastening will be discussed in the context of the disclosed embodiments. Those skilled in the art will recognize known substitutes for the material, manufacturing methods, and fastening methods, all of which are contemplated as compatible with the disclosed embodiments and are intended to be encompassed by the appended claims.

Referring to FIG. 1, in use, the system 100 is mounted to a wall and may be color-coded yellow to indicate that the system 100 is adapted for biohazardous bodily materials and/or fluids, such as vomit, feces and/or urine. In one embodiment, the packaging of the system 100 includes the following: an 8 ounce bag of sanitizing powder (not shown), two 2 ounce bottles of a disinfectant (not shown), an instruction sheet (not shown), a biohazard bag (container) with a twist tie (not shown), Nitrile™ gloves (not shown), an eye/face shield (not shown), a disposable gown (not shown), shoe covers (not shown), an antiseptic towelette (not shown), a receptacle 110 and a bag of modular components 10 for assembling the modular implements 15.

The modular implements 15 are intended to keep users at a safe distance from the above-mentioned potentially hazardous material. The modular implements 15 may be partially disassembled to essentially provide hands-free cleanup and safe disposal after usage. When disassembled, the modular implements 15 are placed in a biohazard bag.

Figure 2:
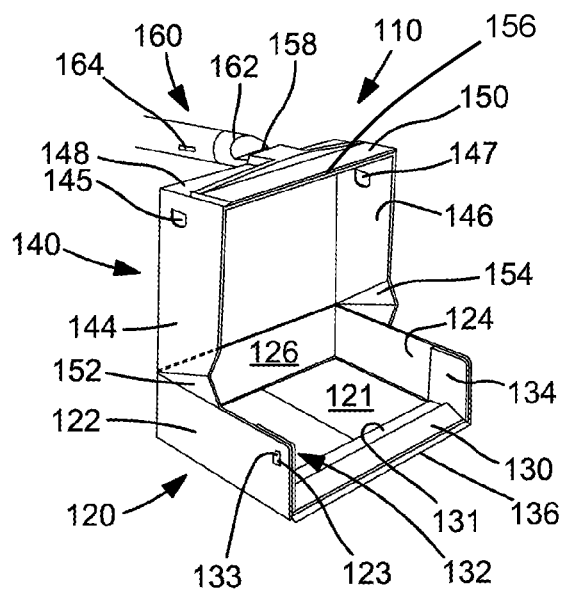
FIG. 2 is a fragmentary perspective view of a receptacle of the system of FIG. 1 illustrated in an opened position.
Figure 3:
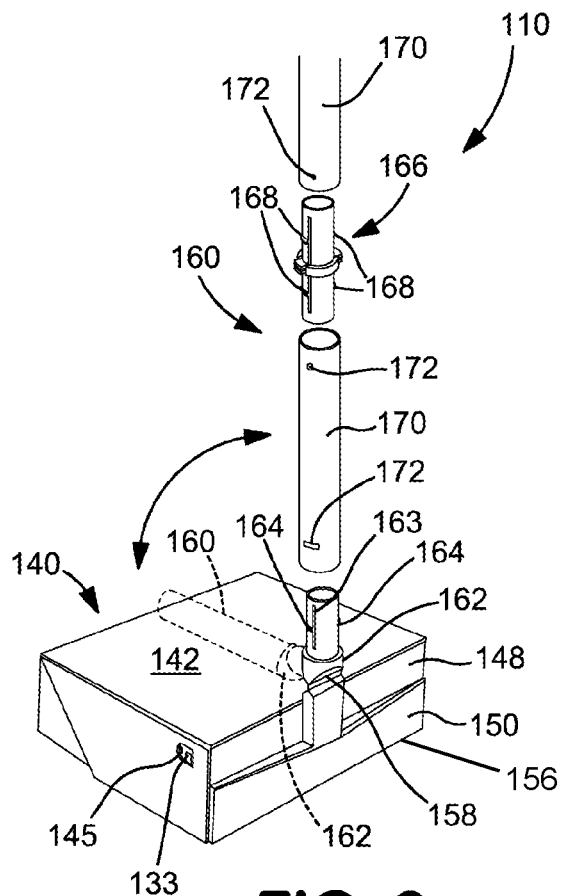
FIG. 3 is a perspective view, partly exploded and partly in phantom, of the receptacle of FIG. 2 in a closed position.
Figure 4:
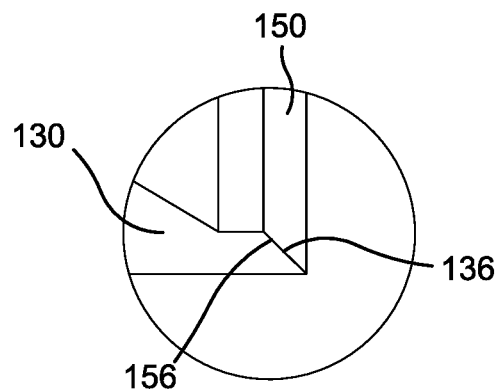
FIG. 4 is an enlarged fragmentary side view of the closed position of the receptacle of FIG. 2 illustrating a sealing relationship in the closed position.
Figure 5:
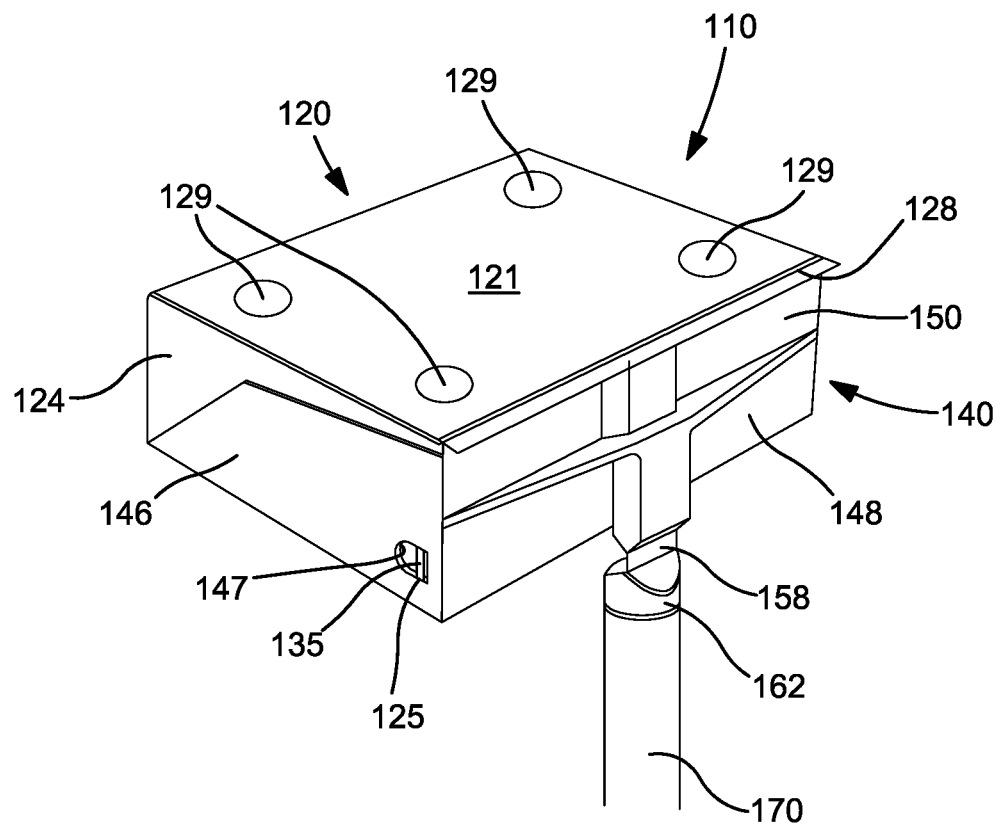
FIG. 5 is an obverse fragmentary perspective view of the receptacle of FIG. 2 illustrated in the closed position.

As illustrated in FIGS. 2 and 3, the receptacle 110 comprises a base 120, a cover 140 and a modular handle assembly 160. In the disclosed embodiment, the base 120 and cover 140 are integrally joined and are constructed of corrugated paperboard, cardboard and/or other semi-rigid fibrous material but a person having ordinary skill in the art would appreciate that other materials are compatible with the disclosed system 100. The base 120 and the cover 140 function to form an enclosure which houses various materials and tools, such as the modular components 10 for assembling the modular implements 15, in a pre-usage configuration and is ultimately openable to access the materials and the tools and to employ the receptacle 110 in a spill removal and disposal process. The receptacle 110 ultimately functions as the depository for the disposal of the biohazardous material and is transformable to a secure closed position, as illustrated in FIG. 3, for final disposal.

As shown in FIGS. 2-5, the base 120 has a generally rectilinear shape with a bottom panel 121, two opposed upright side panels 122, 124, an upright rear panel 126 and an open front forming a lower front edge 128. The side panels 122, 124 each have an aligned opening 123, 125, respectively. The bottom panel 121 preferably has a double ply construction. An underside of the base 120 has four pressure-sensitive vinyl anti-skid feet 129 which prevent or reduce sliding of the base 120 across a surface.

An injection molded bottom edge insert 130 traverses a lateral width of the bottom panel 121 and has a rearwardly disposed elevated lip 131 which functions as a material retainer. The insert 130 includes opposed upright shoulders 132, 134 which are inwardly deflectable and integrally mount outwardly projecting barbs 133, 135. The shoulders 132, 134 of the insert 130 snugly engage against the side panels 122, 124, respectively. The barbs 133, 135 project through the respective openings 123, 125. A frontal edge 136 of the insert 130 is angled or slanted. The insert 130 functions to impose rigidity to the base 120 and, in particular, the frontal edge 136 which contacts the floor during usage.

The cover 140 includes a top panel 142, opposed side panels 144, 146, and a front panel 148 which forms a quasi-rectangular lid for the base 120. A rear of the top panel 142 integrally connects with the rear panel 126 of the base 120 and forms a flexible pivotal connection therewith. The side panels 144, 146 have aligned apertures 145, 147, respectively.

Integral gussets 152, 154 are scored and perforated and connect between the side panels 122, 124 of the base 120 and the side panels 142, 144 of the cover 140. The gussets 152, 154 create a bistable, over-center configuration which functions to keep the cover 140 stable in an open (first) position (see FIG. 2) and a closed (second) position (see FIG. 3). In the open position, the cover 140 is substantially perpendicular to the base 120. In the closed position, the cover 140 is substantially parallel to the base 120. Pivoting the cover 140 over the base 120 from the open position to the closed position causes the gussets 152, 154 to facilitate a closure bias to urge the cover 140 to the closed position.

An injection molded mounting bracket 150 is affixed to the front panel 148. In the disclosed embodiment, the insert 130 and the bracket 150 are constructed of an injection molded plastic but a person having ordinary skill in the art would appreciate that other materials and methods of manufacture may be compatible with the system 100. The bracket 150 has a narrow forwardly extending skirt that forms an angled or inclined edge 156. The bracket 150 includes a medial extension which forms a living hinge 158 that integrally connects with a connector 162. The connector 162 and living hinge 158 allow the connector 162 and handle assembly 160 to lie on a top surface of the top panel 142 (see FIG. 3). The connector 162 includes two pairs of longitudinal slots 163 which form a resilient medial portion for carrying a pair of opposing retention tabs 164.

A spiral wound paperboard tube 170 having a length of approximately 12 inches includes longitudinally spaced pairs of opposing slots 172 which, upon suitable angular alignment, allow the tabs 164 to snap into the slots 172 to connect the tube to the connector 162. A connector 166 also includes two pairs of longitudinally spaced pairs of tabs 168 which are resiliently outwardly urged. The tabs 168 are secured in the upper slots 172 of the tube 170 and a second substantially identical tube 170 snaps over the upper tabs 168. Additional connectors 166 and tubes 170 may be employed as previously described.

It will also be appreciated that, as best illustrated by the arrows and broken lines in FIG. 3, that the living hinge 158 allows the handle assembly 160 to be manipulated to facilitate the positioning, usage, and closing of the receptacle 110 in the disposal process.

Once the handle assembly 160 is mounted and assembled to the cover 140, the receptacle 110 is ready for usage and is positionable adjacent the spill to be removed. A liquid absorbing composition (not illustrated) may be poured onto the spill. The spill material is swept into the base 120 past the interior retainer lip 131 where it may optionally be exposed to sanitizer (not illustrated) within the base 120. The cover 140 is then pivoted downwardly over the base 120 to enclose the open front portion of the base 120 so that the inclined mounting bracket edge 156 and the lower front edge 136 of the base 120 closely engage, as best illustrated in FIG. 3.

When the cover 140 is in the closed position over the base 120, the barbs 133, 135 project through the apertures 145, 147 at the sides of the cover 140 to secure the cover 140 and base 120 in the closed position. During this process, the gussets 152, 154 fold over and deflect to create the over-center condition which essentially urges the cover to the closing and locking position (secured by the barbs 133, 135). The cover 140 may be released to open the receptacle 110 by pushing inwardly on the opposed base sides 122, 124 to release the locking barbs 133, 135 from the apertures 145, 147.

After the biohazardous material is secured in the receptacle 110, the handle assembly 160 and the modular implements 15 are disassembled and the receptacle 110 and modular components 10 are placed in a biohazard bag along with any gloves and/or other materials. The biohazard bag is safely secured and placed in disposal. The biohazard bag may be initially packaged within the pre-usage closed receptacle 110.

Figure 6:
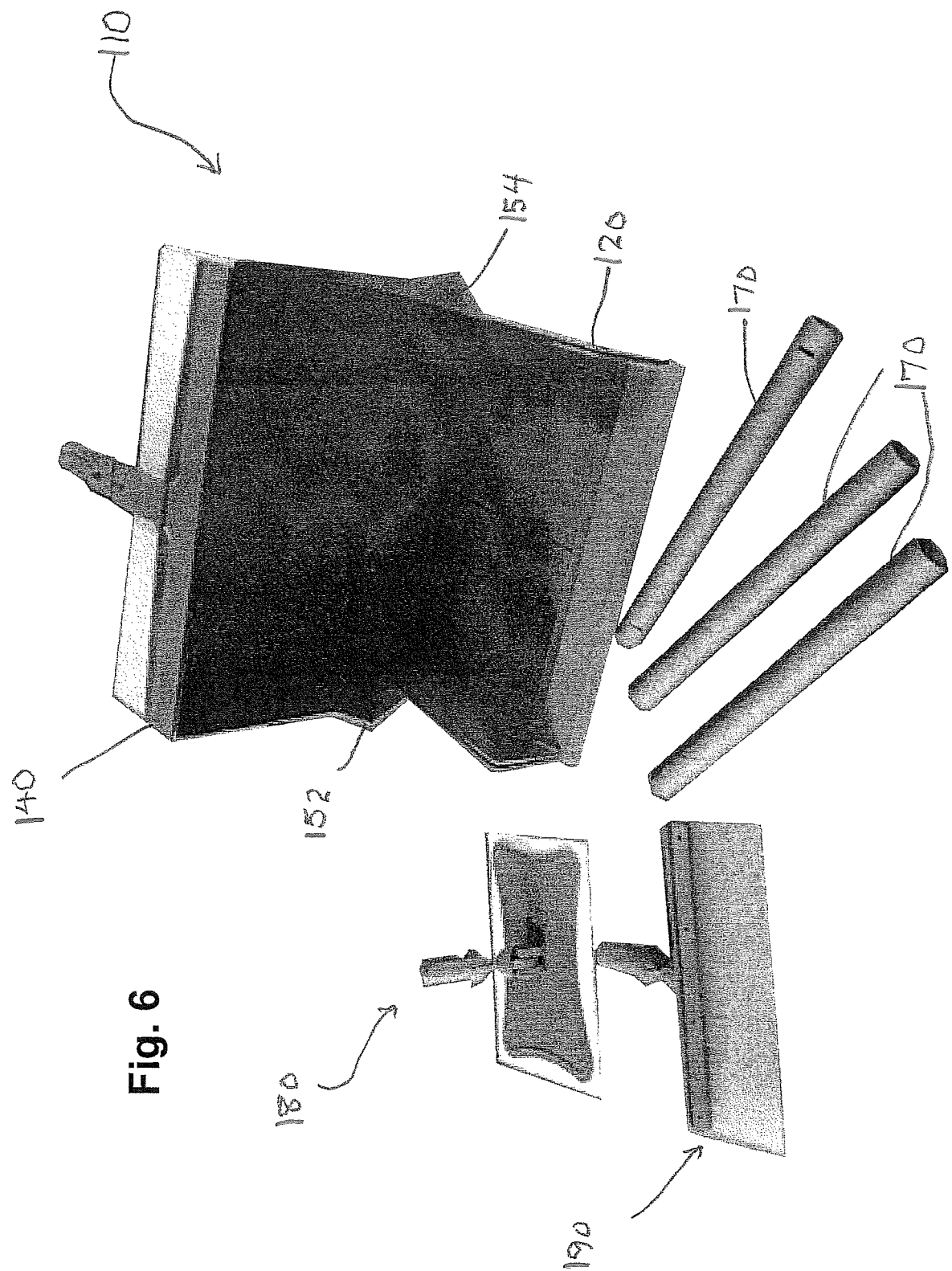
FIG. 6 is a photograph of the receptacle of FIG. 2 in the opened position with selected modular components which may be employed in the system.
Figure 7:
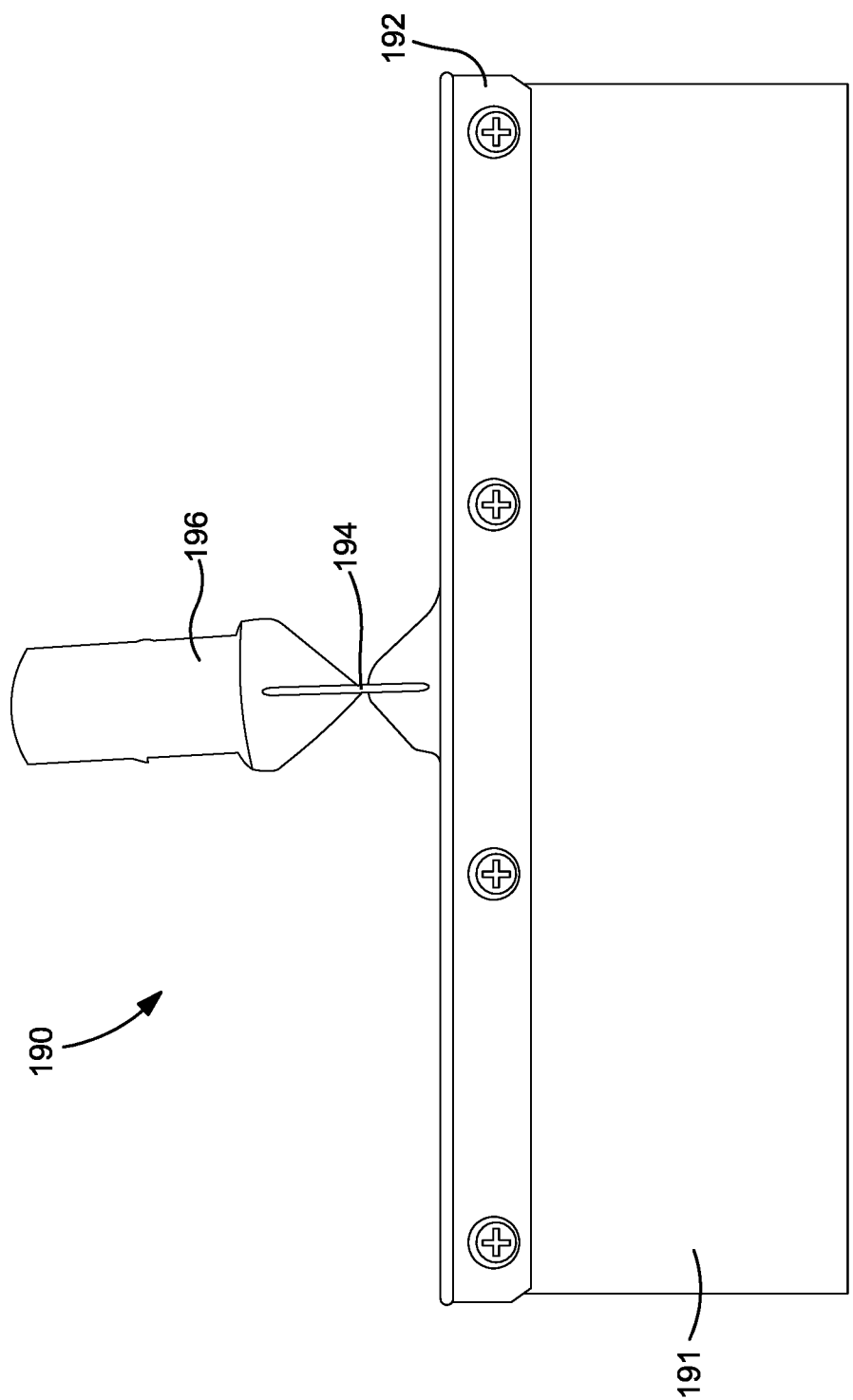
FIG. 7 is an elevated front view of a wiper blade which may be employed in the system of FIG. 1.

As shown in FIGS. 6 and 7 of the disclosed embodiment, in its initial closed position, the receptacle 110 may comprise the bag of disposable modular components 10 that allow for the assembly and proper disposal of the modular implements 15. In the disclosed embodiment, the modular implements 15 include the handle assembly 160, a mop 180 comprising a mop head 182 and a mop pad 184, and a wiper blade 190. It should be appreciated that both the mop 180 and the wiper blade 190 may use the same tubes 170 and connectors 162, 166 previously described with respect to the handle assembly 160 which may, upon usage, be disassembled and discarded as described above.

Referring to FIG. 7, the wiper blade 190 includes a semi-flexible blade-like component 191 which is sandwiched between a pair of mounting brackets 192. The brackets 192 connect via a living hinge 194 to a connector 196 that has substantially the same structure and functions of the connector 162. As previously described, the connector 196 engages the tube 170 as the tabs 168 snap into the slots 172. It will be appreciated that the receptacle 110 functions as a container for all of the modular implements 15 and materials required for a spill cleanup and ultimate disposal.

With reference to FIGS. 8-17, the modular implements 15 may further include a disposable modular broom 220, 220A, a disposable modular dustpan 240 and a disposable modular mop 260, 260A. The disclosed broom 220, dustpan 240 and mop 260, 260A are assembled and selectively used to clean the above-mentioned biohazardous material.

Figure 8:
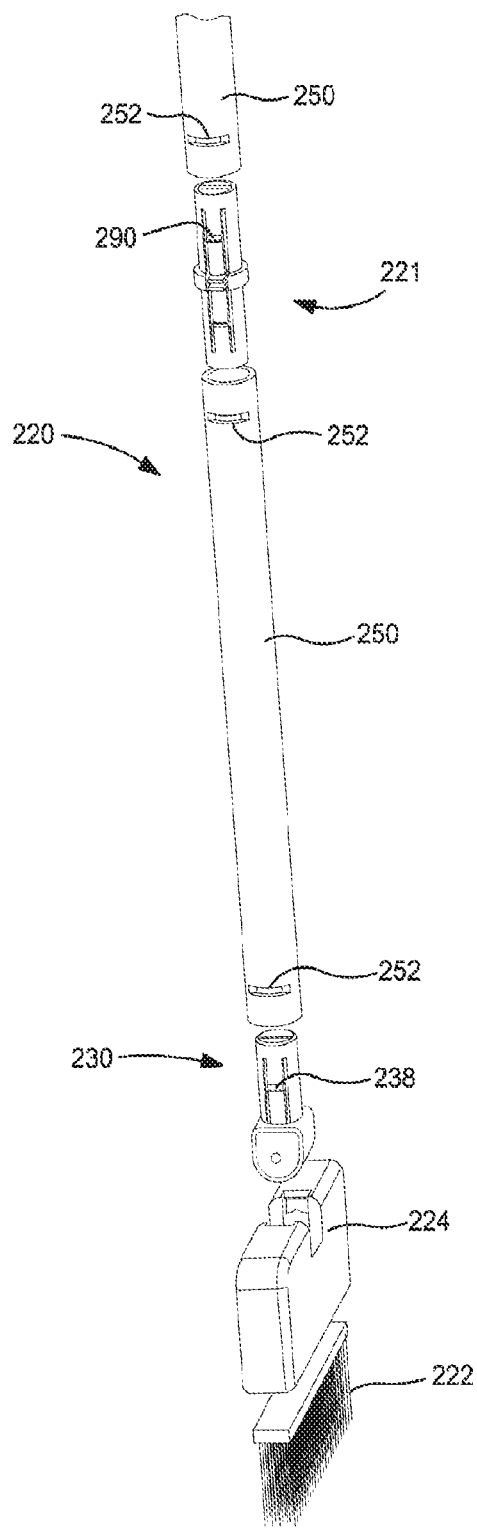
FIG. 8 is an exploded perspective view of a first embodiment of a disposable modular broom which may be employed in the system of FIG. 1.
Figure 8A:
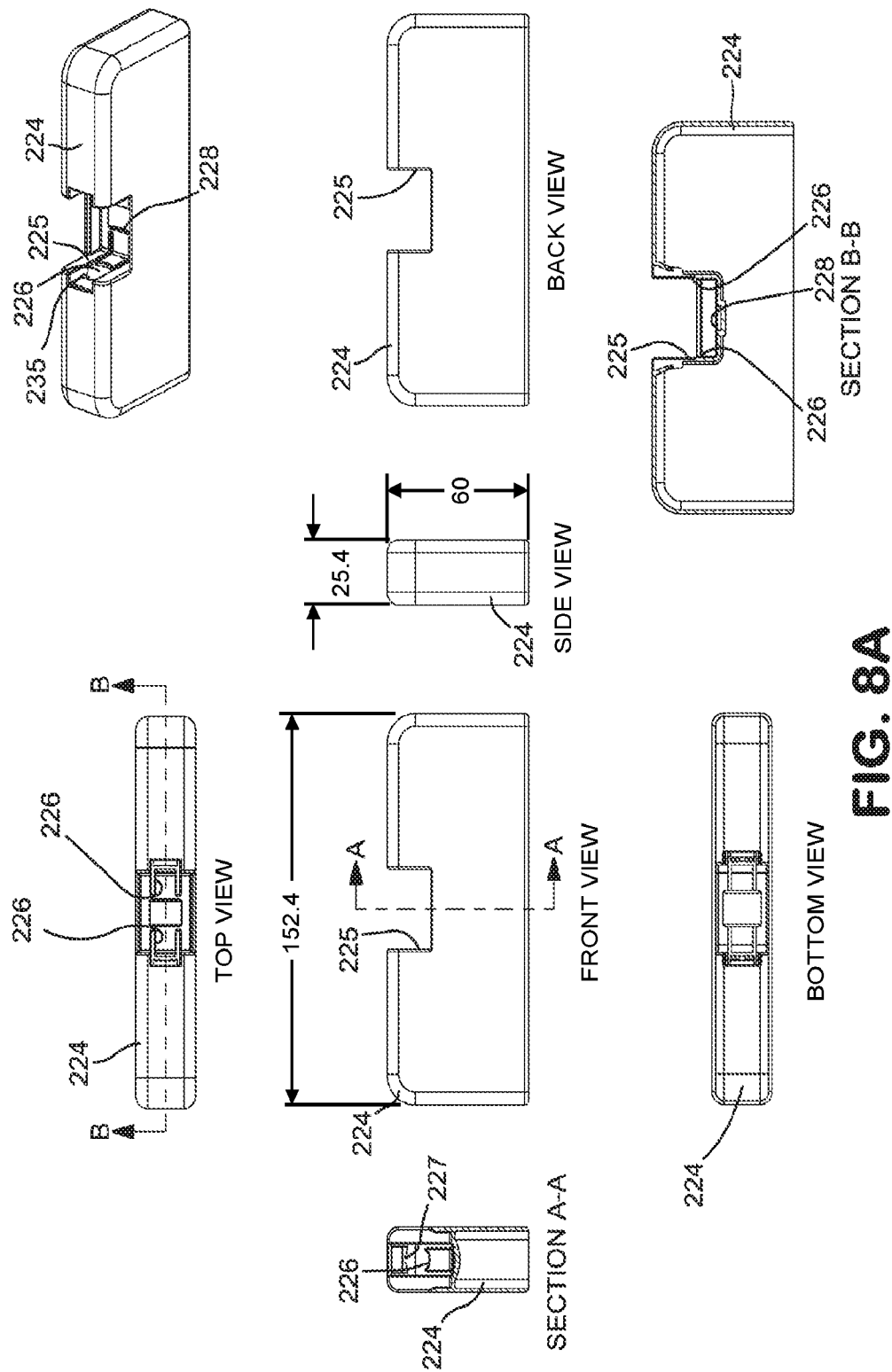
FIG. 8A is an annotated drawing, partly diagrammatic, illustrating a broom housing for the broom embodiment of FIG. 8.
Figure 8B:
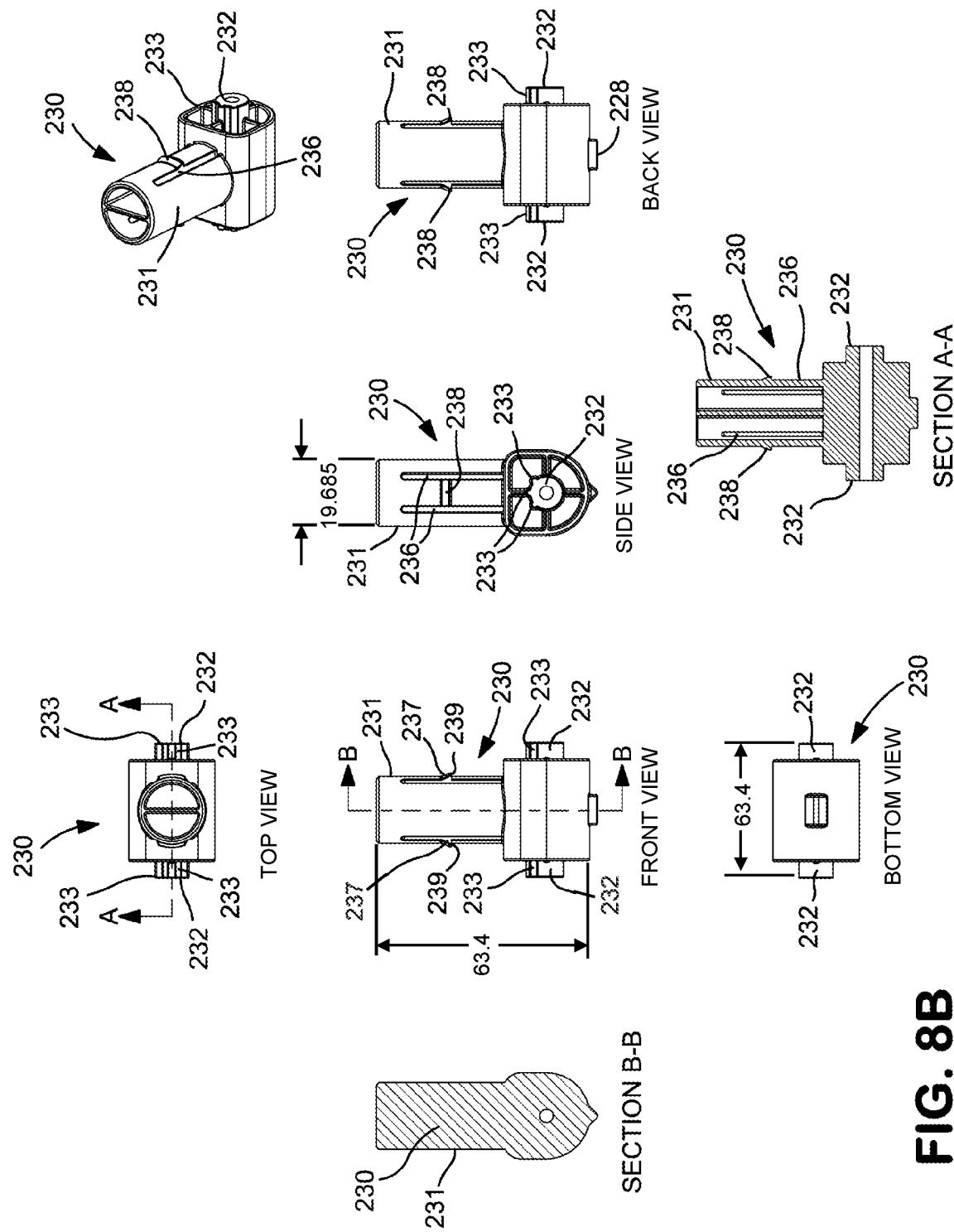
FIG. 8B is an annotated drawing, partly diagrammatic, illustrating various views for a broom pivot of the broom of FIG. 8.

With reference to FIGS. 8-8B, a first embodiment of the broom 220 comprises a bristle assembly 222 received in a housing 224. The housing 224 connects with a first tube 250 via a pivot connector 230 and the first tube 250 connects via one or more connectors 290 to one or more additional tubes 250 in linear succession to form a handle 221.

The broom 220 is tiltable between a straight position and a tilted position by essentially pushing down on the broom 220 and moving the broom 220 to the proper angle. As best illustrated in FIG. 8A, the housing 224 includes a central opening 225 for receiving the pivot connector 230. A pair of laterally disposed yokes 226 receives the pivot connector 230. The pivot connector 230 has a pair of opposed pivots 232 which are received in the yokes 226 and a lower integral retainer pawl 234 which is received in a detent 228 at the bottom of the housing 224. As best illustrated in FIG. 8B, the pivots 232 include angularly spaced index ribs 233 which selectively engage in one or more selective detents 227 at the opposed locations of the yokes 226 of the housing 224. An integral spring 229 (see FIG. 2C) biases the ribs 233 to lock into the detents 227.

The pawl 234 and ribs 233 may be received in selective detents 227 in the upper portion of the yoke 226 to provide a stable position broom 220 configuration. When the pawl 234 is received in the lower central detent 228, the connector 230 is oriented in a vertical or straight position. When the ribs 233 are received in selective off-angle detents 227, the connector 230 and the handle 221 are fixed at a stable angle to the housing 224. The angular position may be relatively easily fixed by pushing down on the tubes 250 which form the handle 221 and rotating to the proper angular position.

The upper portion of the pivot connector 230 forms a quasi-cylindrical structure 231 with longitudinal slots 36 at opposed sides of a pair of opposed projecting barb-like retention tabs 238. A tube 250 which has corresponding opposed circumferential slots 252 may be aligned and forced over the connector 290 until the tabs 238 engage into the slots 252. The opposed tabs 238 are inwardly depressible due to flexure of tube 250 provided by the configuration of the slots 252. Each tab 238 has a ramp 237 to facilitate sliding of the tube 250 over the tab 238 and a radial engagement edge 239 to engage an edge of the slot 250 and prevent withdrawal. The tabs 238 and slots 252 are dimensioned and alignable so that the tabs 238 are lockingly received in the slots 252. Once engaged, the connection between the pivot connector 230 and the tube 250 is essentially a one-way connection, and disassembly of the tube 250 from the pivot connector 230 is practically precluded.

Figure 9:
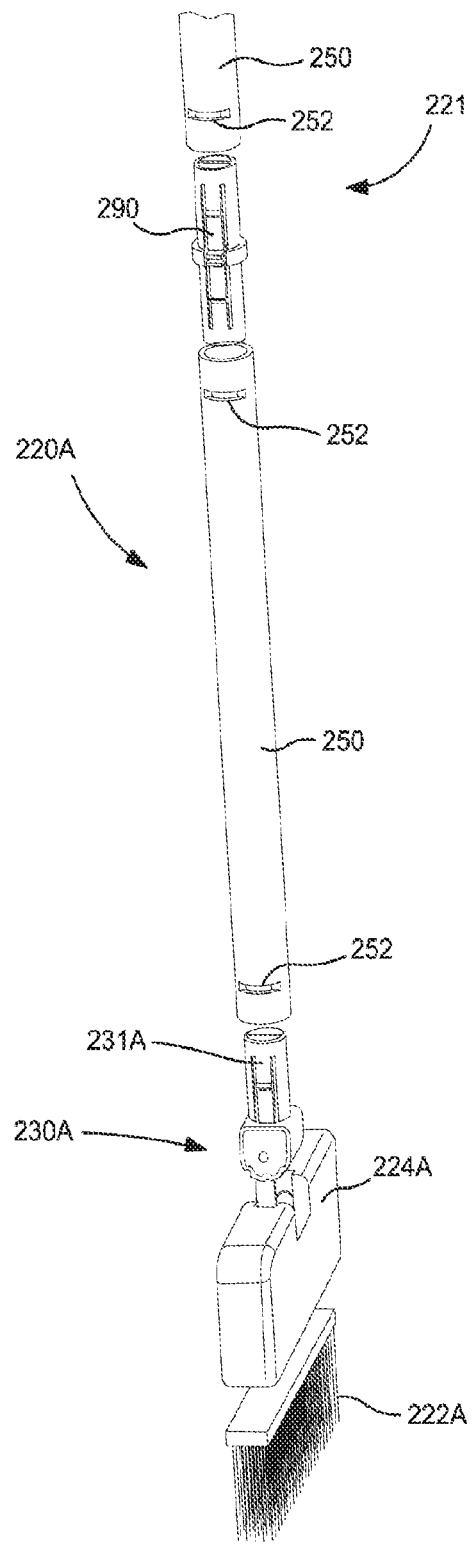
FIG. 9 is an exploded perspective view of a second embodiment of a disposable modular broom which may be employed in the system of FIG. 1.
Figure 9A:
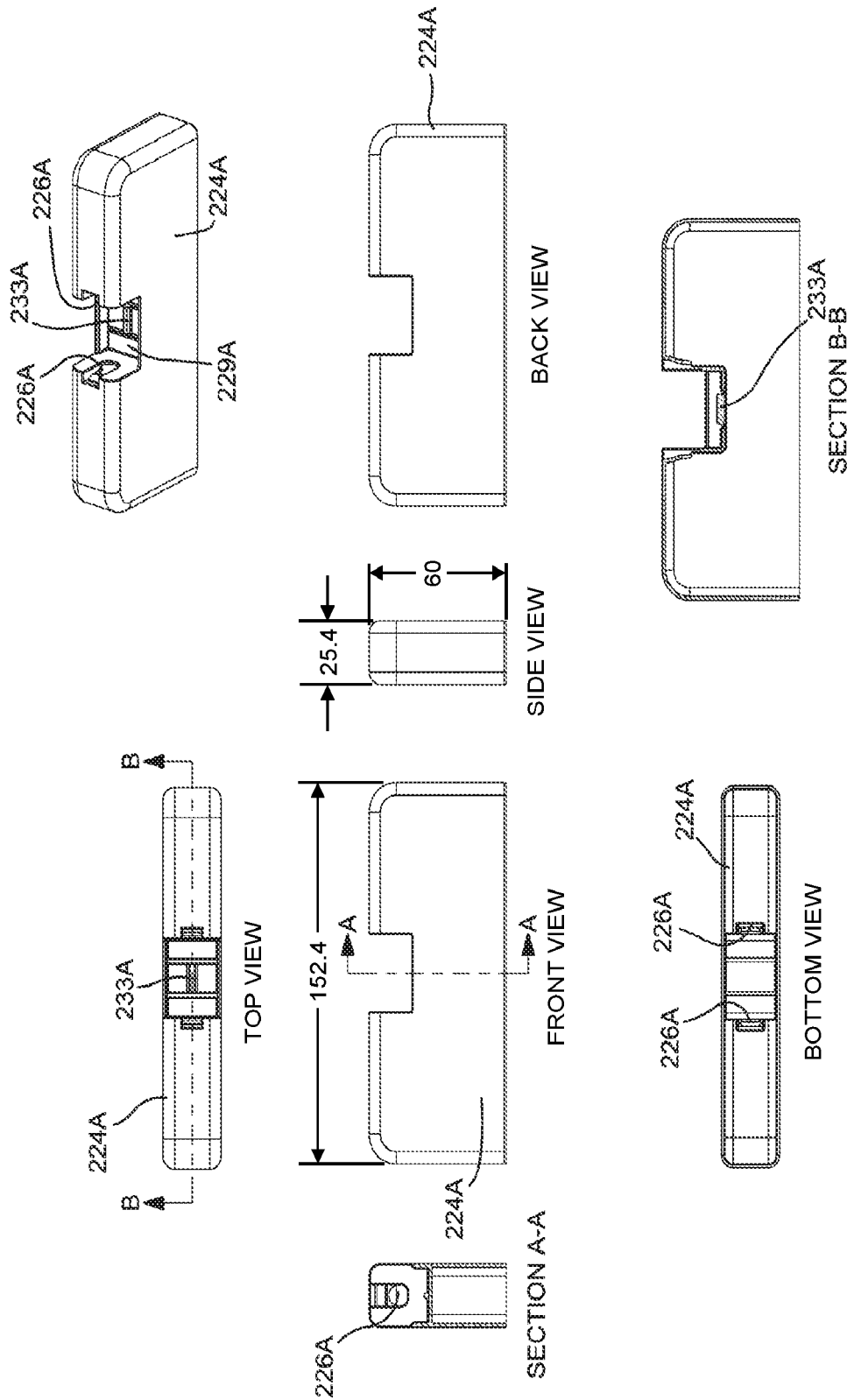
FIG. 9A is an annotated drawing, partly diagrammatic, illustrating various views of a housing for the broom embodiment of FIG. 9.
Figure 9B:
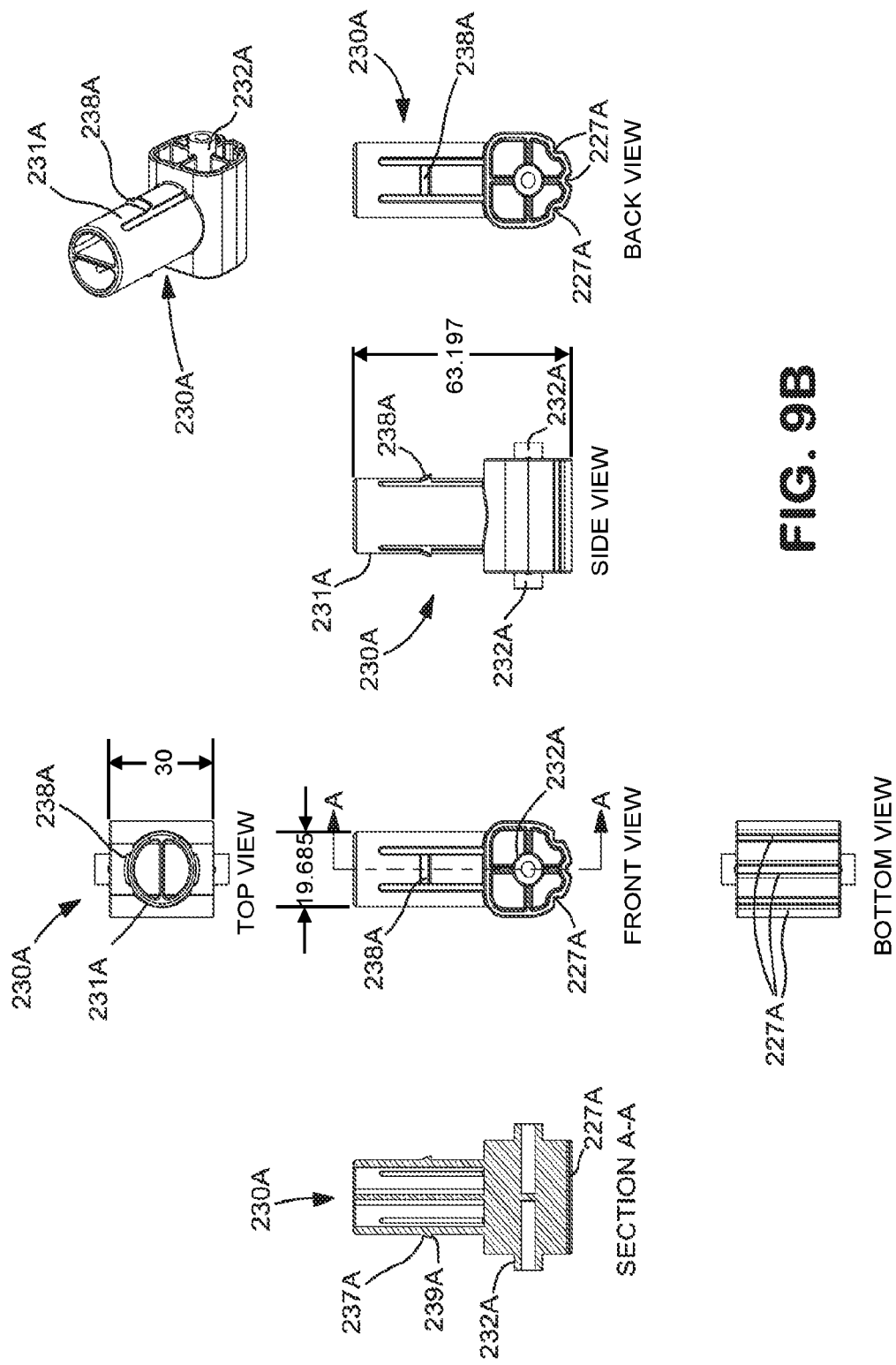
FIG. 9B is an annotated drawing, partly diagrammatic, illustrating various views for a broom pivot of FIG. 9.

A second embodiment of a broom 220A is illustrated by FIGS. 9-9B. Corresponding components of the broom 220A are designated with the same numerals as that for broom 220 except for a trailing alphabetic numeral "A." Opposed pivots 232A are received in a pair of laterally disposed yokes 226A. A relationship between index ribs 233A and detents 227 is essentially reversed for broom 220A in relation to broom 220 in that the detents 227A are formed on a bottom portion of a rotatable pivot 230A, and the detents 227A are engaged by upwardly projecting pawls 234A or ribs 233A.

An upper portion 231A of the pivot connector 230A is generally similar to that described for the pivot connector 230 of the broom 220. The pivot connector 230A includes a pair of opposed depressible retainer tabs 238A which are receivable in circumferential slots 252 of the tubes 250. It will be appreciated again that the angular tilt may be provided by essentially pushing down on the broom 220A from a handle 221A and rotating the handle 221A to the proper angular position. An integral spring 229A engages the connector 230A to maintain the engagement between the ribs 233A and the detents 227. A representative tilted position of the broom 220A and a relatively straight position of the broom 220A are best illustrated in FIGS. 3C and 3D, respectively.

Figure 10:
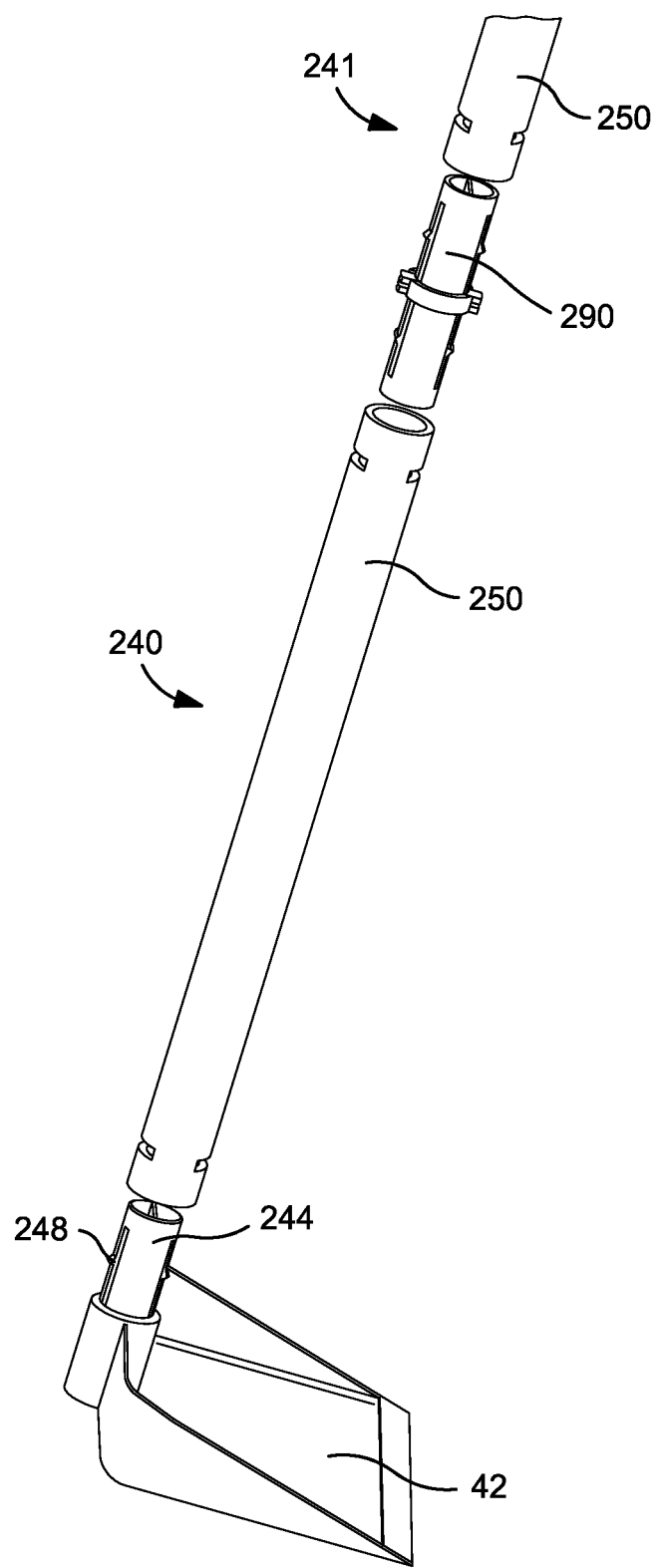
FIG. 10 is an exploded perspective view of a disposable modular dustpan which may be employed in the system of FIG. 1.
Figure 10A:
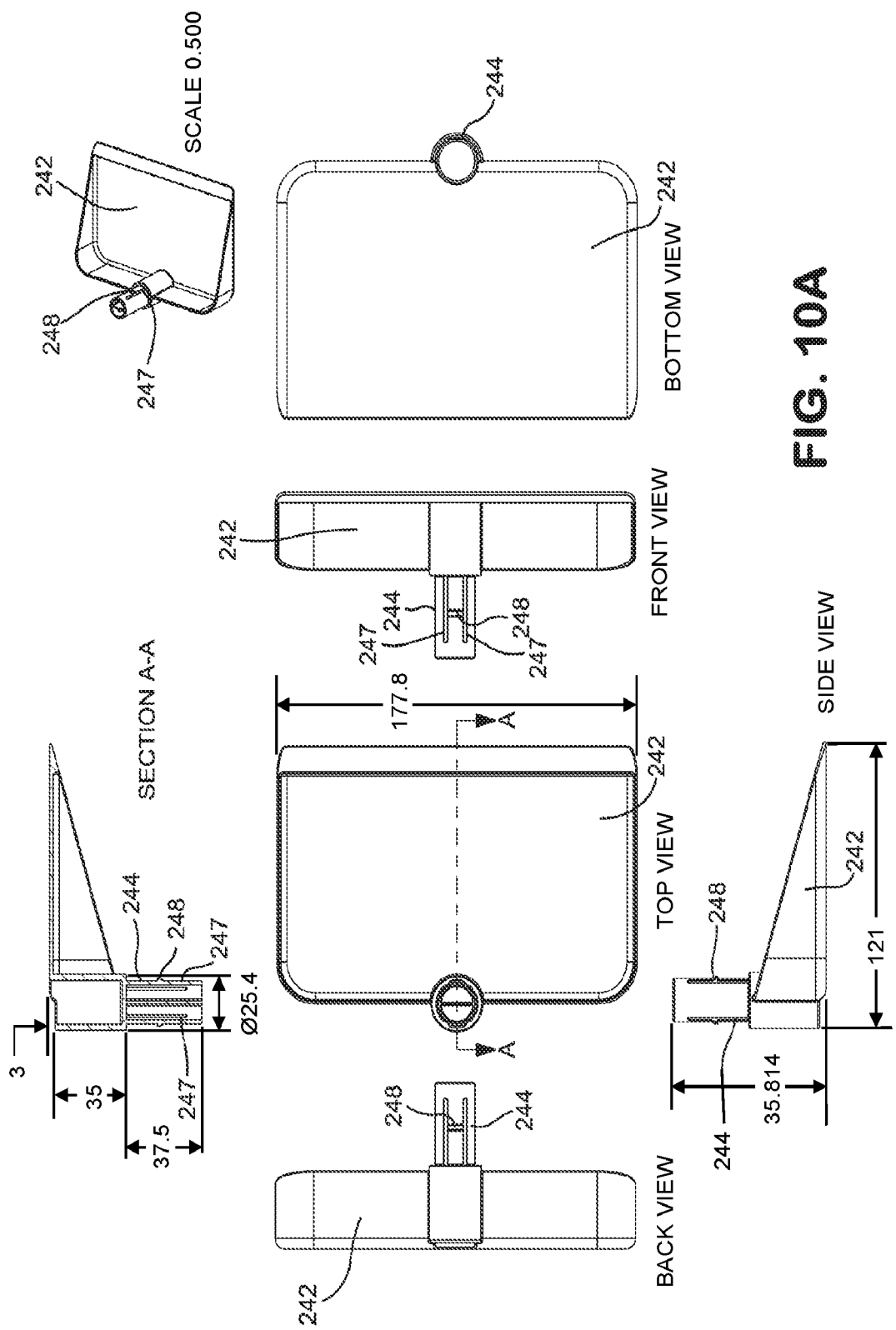
FIG. 10A is an annotated drawing, partly diagrammatic, illustrating various views of a dustpan portion of the dustpan of FIG. 10.

With reference to FIGS. 10-10A, a modular disposable dustpan 240 includes a retainer tray 242 having the form and function of a conventional dustpan. The medial rear of the tray 242 includes a vertically projecting integral stepped cylindrical connector 244. The connector 244 includes a pair of opposed peripheral depressible retainer tabs 248 which project radially. Longitudinal slots 247 on both sides of each tab 248 allow the region around the tabs 248 to flex inwardly. In a normal state, the tabs 248 are biased to project outwardly. The tabs 248 are similar in form and function to tabs 238. A tube 250 may be aligned to slide over the connector 244 so that peripheral slots 252 receive the tabs 248 which project outwardly to retain the tube 250 to the receiving tray 242 in an essentially one-way connection. The upper portion of the tube 250 may receive a connector 290, as will be described below, for connecting additional tubes 250 to provide a handle 241 at a desired length.

Figure 11:
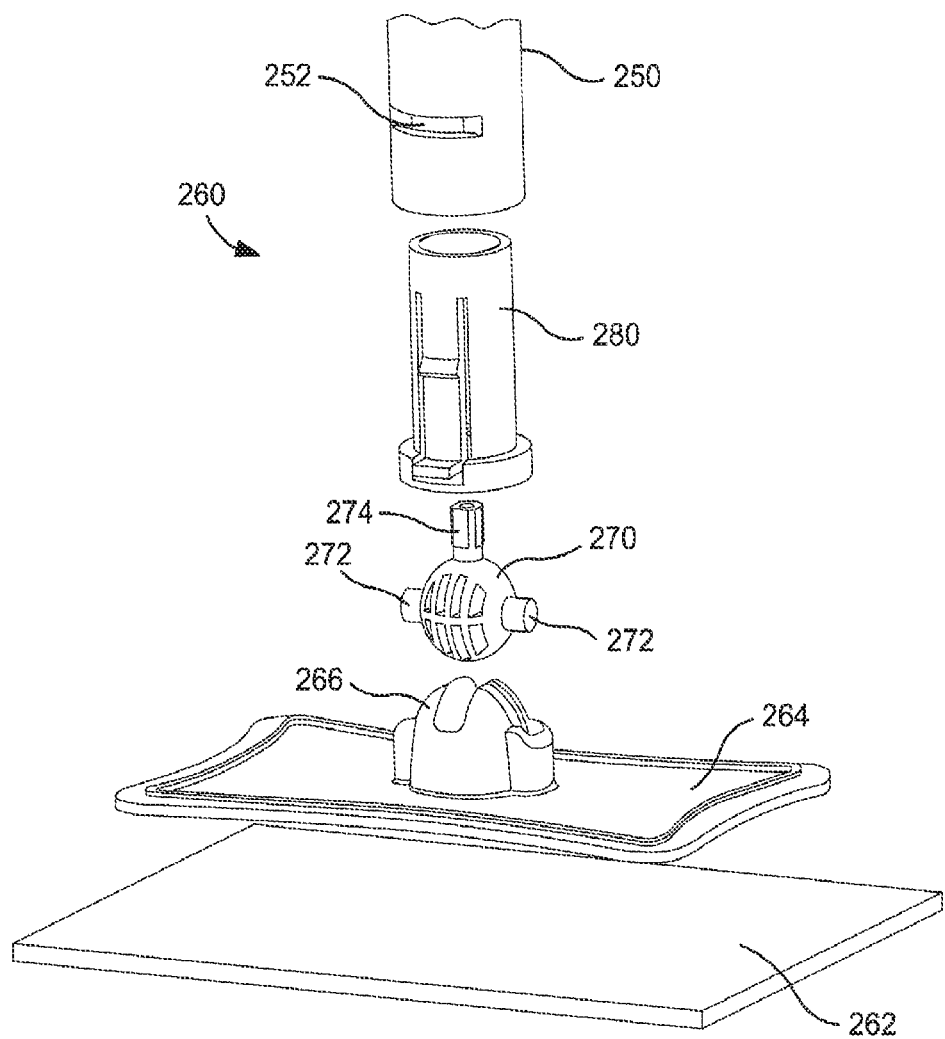
FIG. 11 is a fragmentary exploded perspective view of a first embodiment of a disposable modular mop which may be employed in the system of FIG. 11.
Figure 11A:
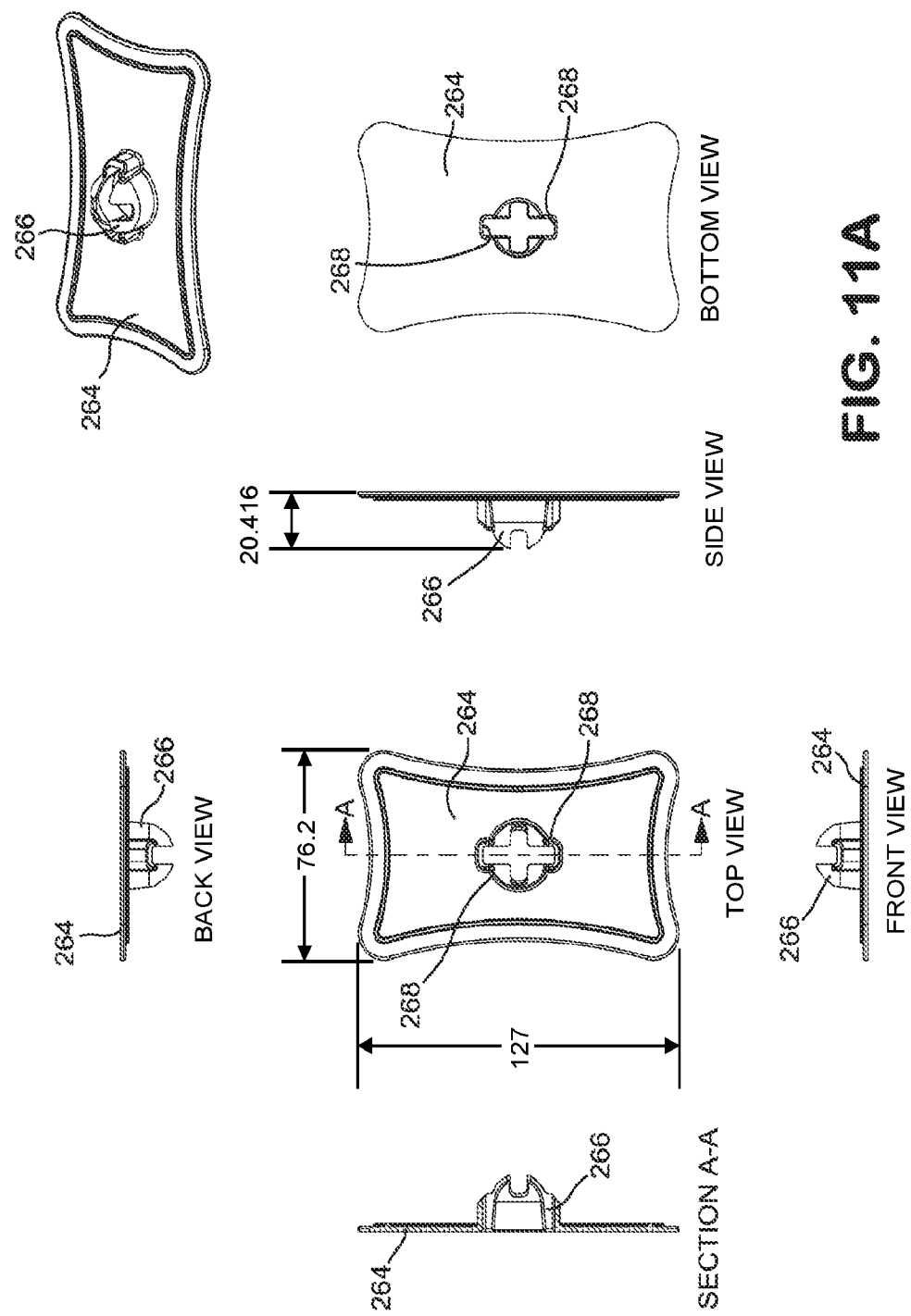
FIG. 11A is an annotated drawing, partly diagrammatic, illustrating various views of a mop/plate ball joint for the mop of FIG. 11.

With reference to FIGS. 11-11B, a modular disposable mop 260 includes a working pad 262, a support plate 264 and an upwardly projecting centrally located ball mount 266 for a pivoting ball member 270. The pad 262 is saturated with disinfectant prior to usage as further described below. The ball mount 266 includes a pair of laterally spaced retainers 268 to secure opposed projecting pivots 272 included on the ball member 270. The ball member 270 also includes a quasi-square shaped elongated mounting stud 274 which is received in a tube connector 280. It will be appreciated that a tube 252 will ultimately be connected to connector 280 in a fixed rotatable position relative to the connector 280 so that the plate 264 and the pad 262 may swivel relative to a flat surface.

Figure 12:
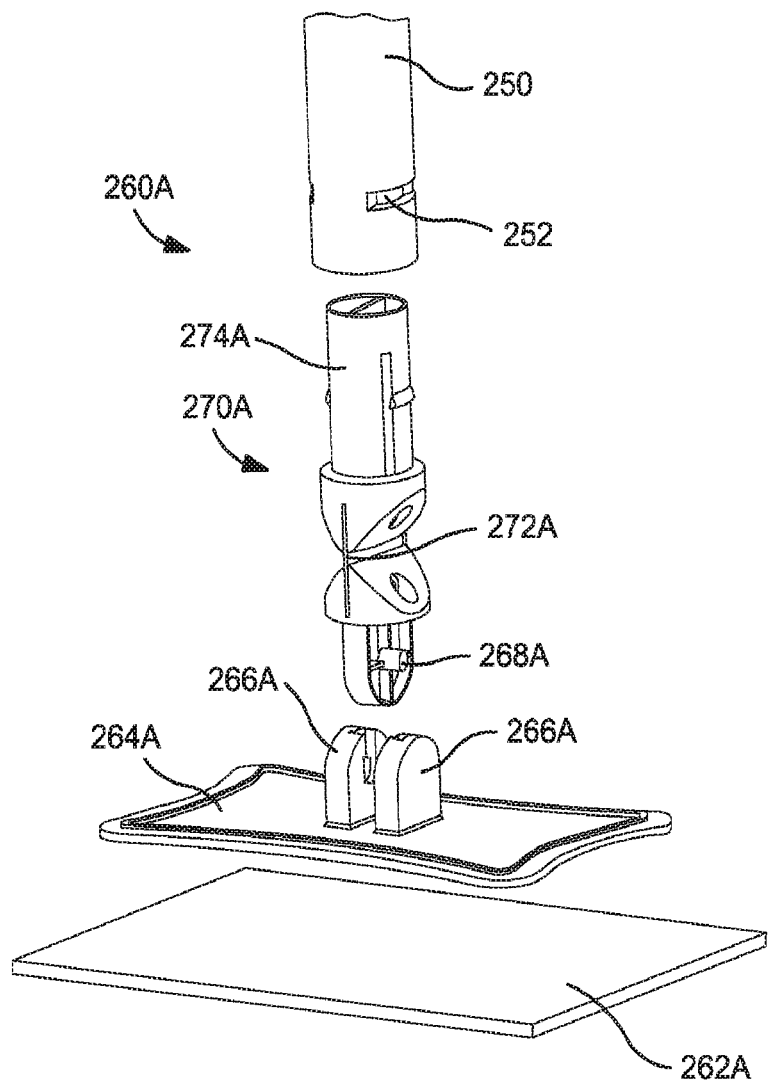
FIG. 12 is a fragmentary exploded perspective view of a second embodiment of a disposable modular mop which may be employed in the system of FIG. 12.
Figure 12A:
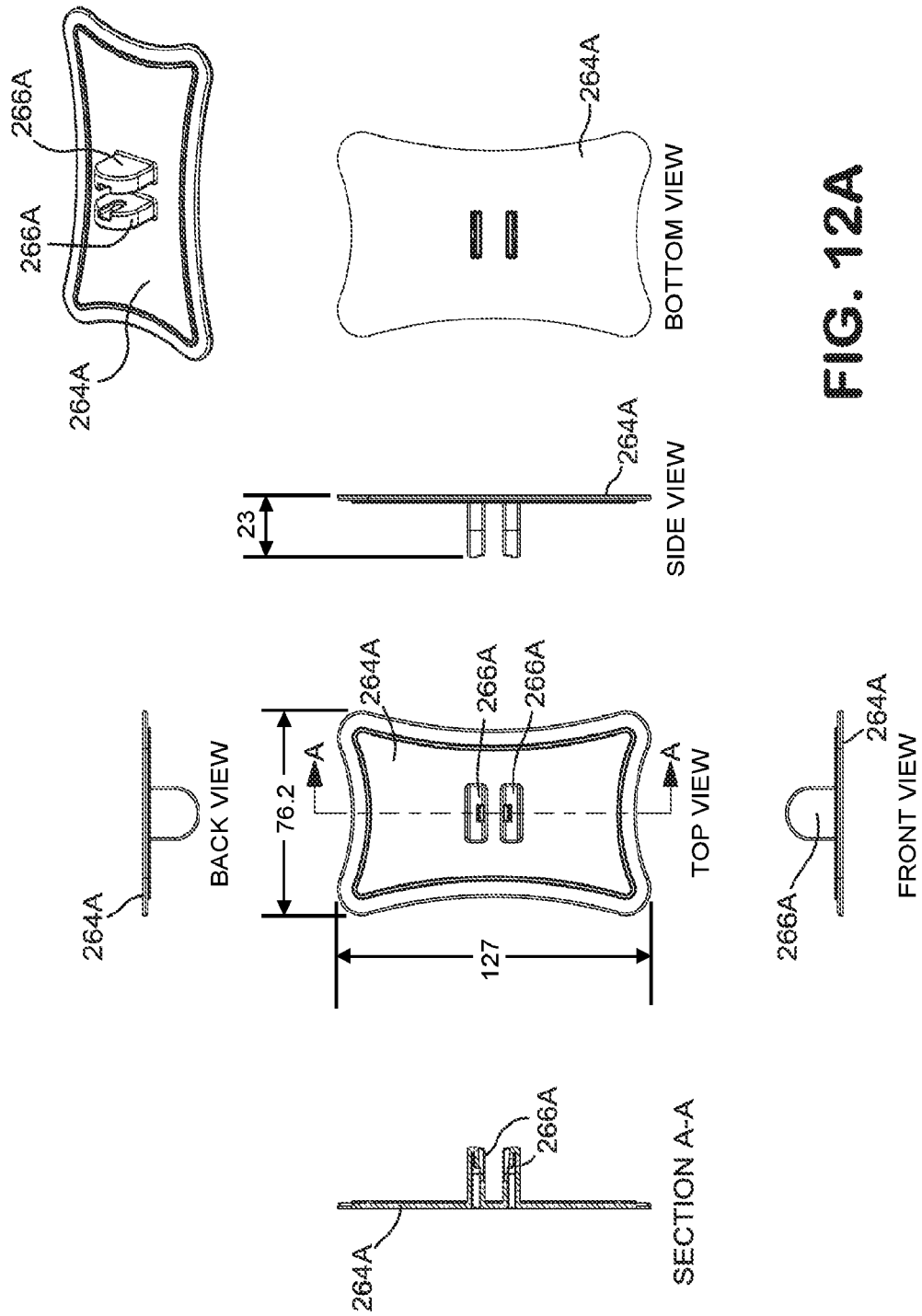
FIG. 12A is an annotated drawing, partly diagrammatic, illustrating various views of a mop plate for the mop of FIG. 12.
Figure 12B:
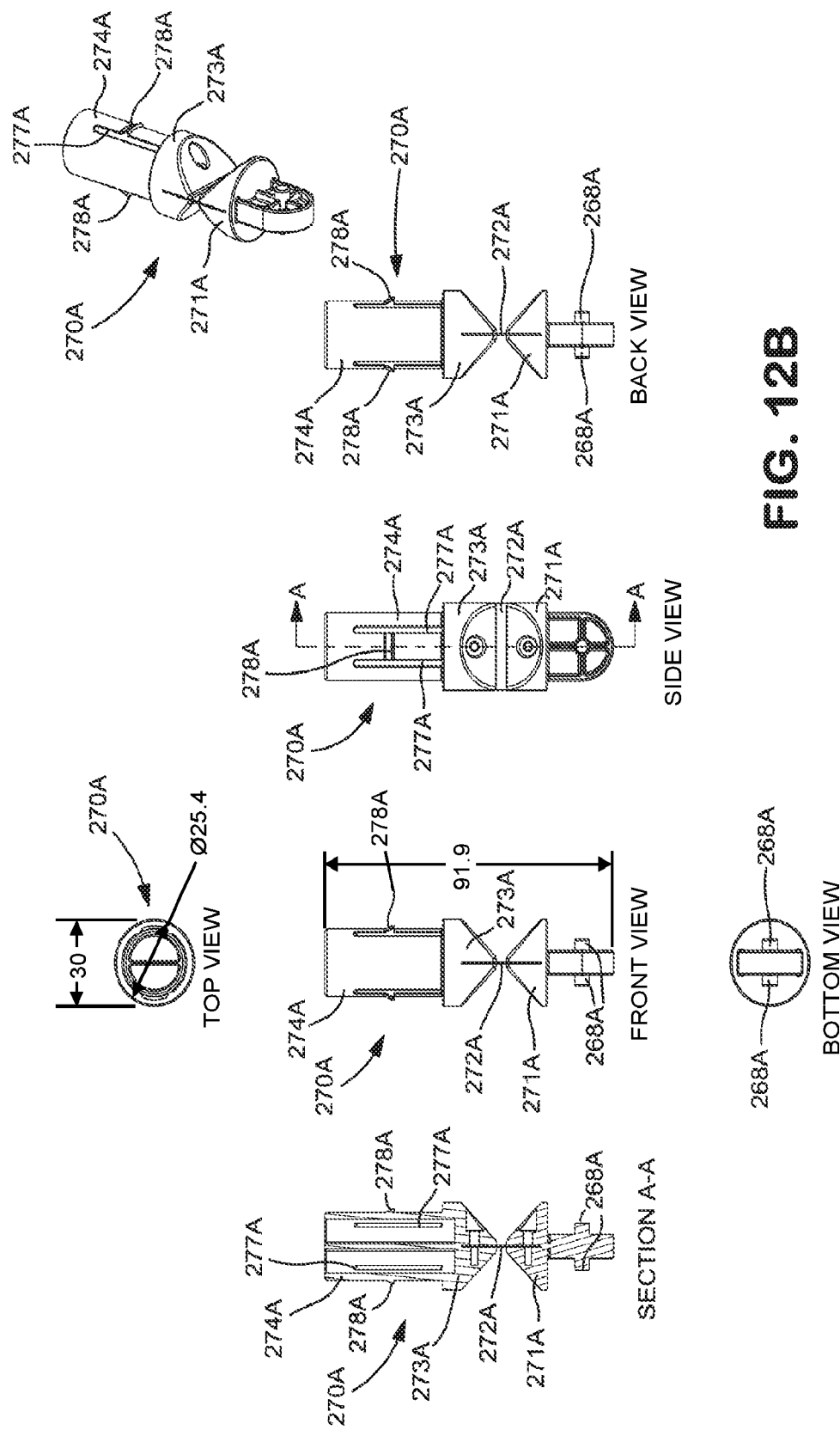
FIG. 12B is an annotated drawing, partly diagrammatic, illustrating various views of a swivel assembly for the mop of FIG. 12.

With reference to FIGS. 12-12E, a second embodiment of a modular disposable mop 260A includes a pad 262A and a support plate 264A. The pad 262A is preferably saturated with disinfectant prior to usage. The support plate 264A includes a pair of upwardly projecting yokes 266A which receive a pair of projecting pivots 268A from a swivel assembly 270A having a living hinge 272A and a connector 274A. The living hinge 272A has a flexible medial portion which allows the connector 274A to pivot. The living hinge 272A may be a separate component or integrally connected to opposed apex structures 271A, 273A which allow for pivoting. It will be appreciated that another axis of pivoting is provided by the pivots 268A. As illustrated in FIGS. 12D and 12E, a handle 261A included on the mop 260A can pivot up to 83° to both a front and rear of the assembled mop 260A and the living hinge 272A can bend up to 90° to the front and rear of the assembled mop 260A.

Figure 12C:
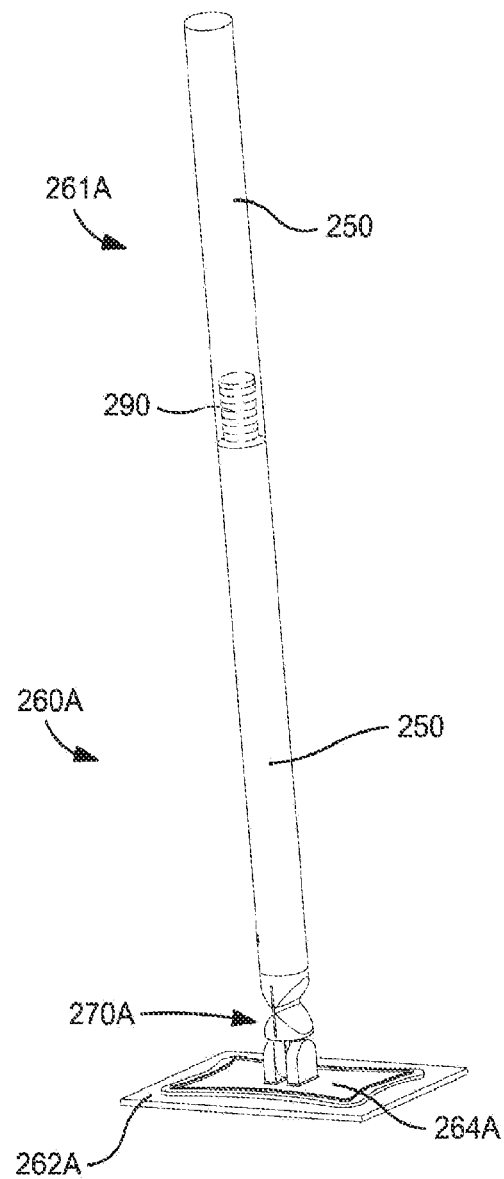
FIG. 12C is a perspective view of the mop of FIG. 12.

An upper portion of the swivel assembly 270A has a generally cylindrical connector 274A which includes a pair of opposed depressible retainer tabs 278A. The tabs 278A are positioned between adjacent longitudinal slots 277A to provide a flexure so that a tube 250 may be aligned to slide over the connector 274A. The tabs 278A are received in peripheral slots 252 of the tube 250 to provide a one-way connection for the tube 250 and the handle 261A of the mop 260A. The tabs 278A have a ramp surface at an upper portion and a generally radial edge at the bottom portion to preclude the tube 250 from being withdrawn from the connector 274A. In a normal state, the tabs 278A are essentially biased to project outwardly into the slots 252. It will be appreciated that additional tubes 250 may be added to the mop by a connector 290, as will be described below, to provide a multi-sectional handle 261A length for the mop 260A, as best illustrated in FIG. 12C.

Figure 13:
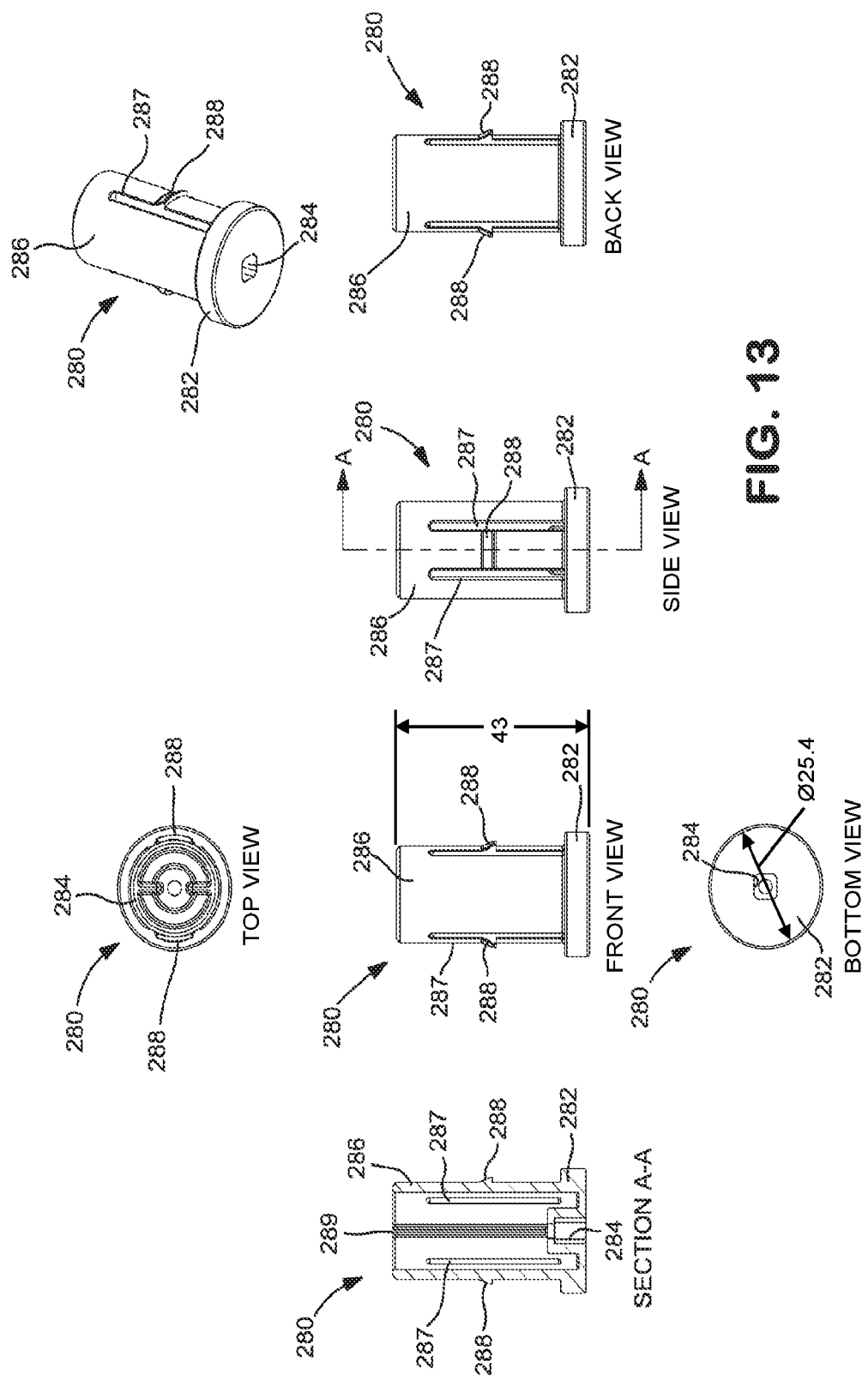
FIG. 13 is an annotated drawing, partly diagrammatic, of a tube connector for the mop of FIG. 11.
Figure 14:
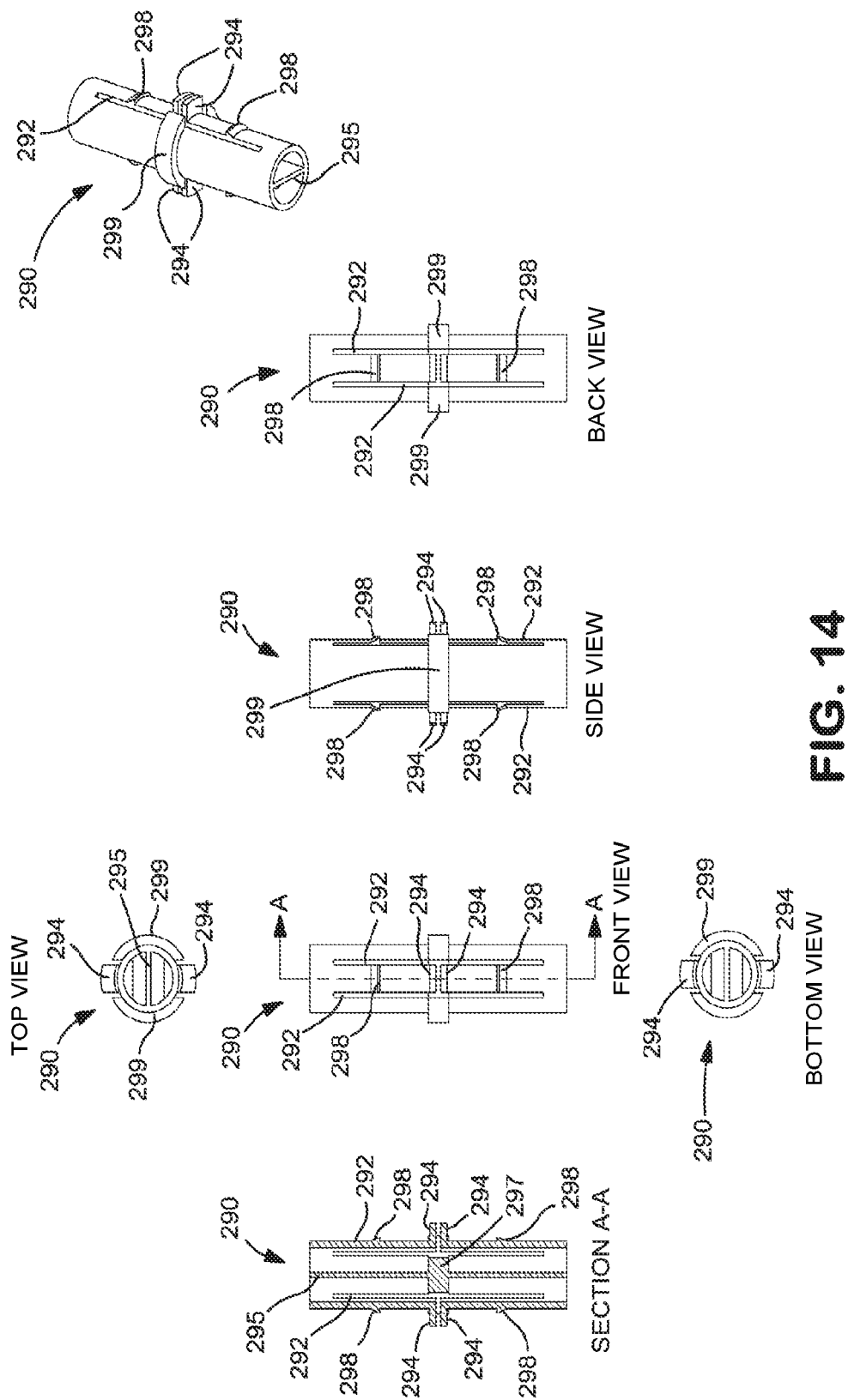
FIG. 14 is an annotated drawing illustrating various views of a tube connector which may be employed in the system of FIG. 1.
Figure 14A:
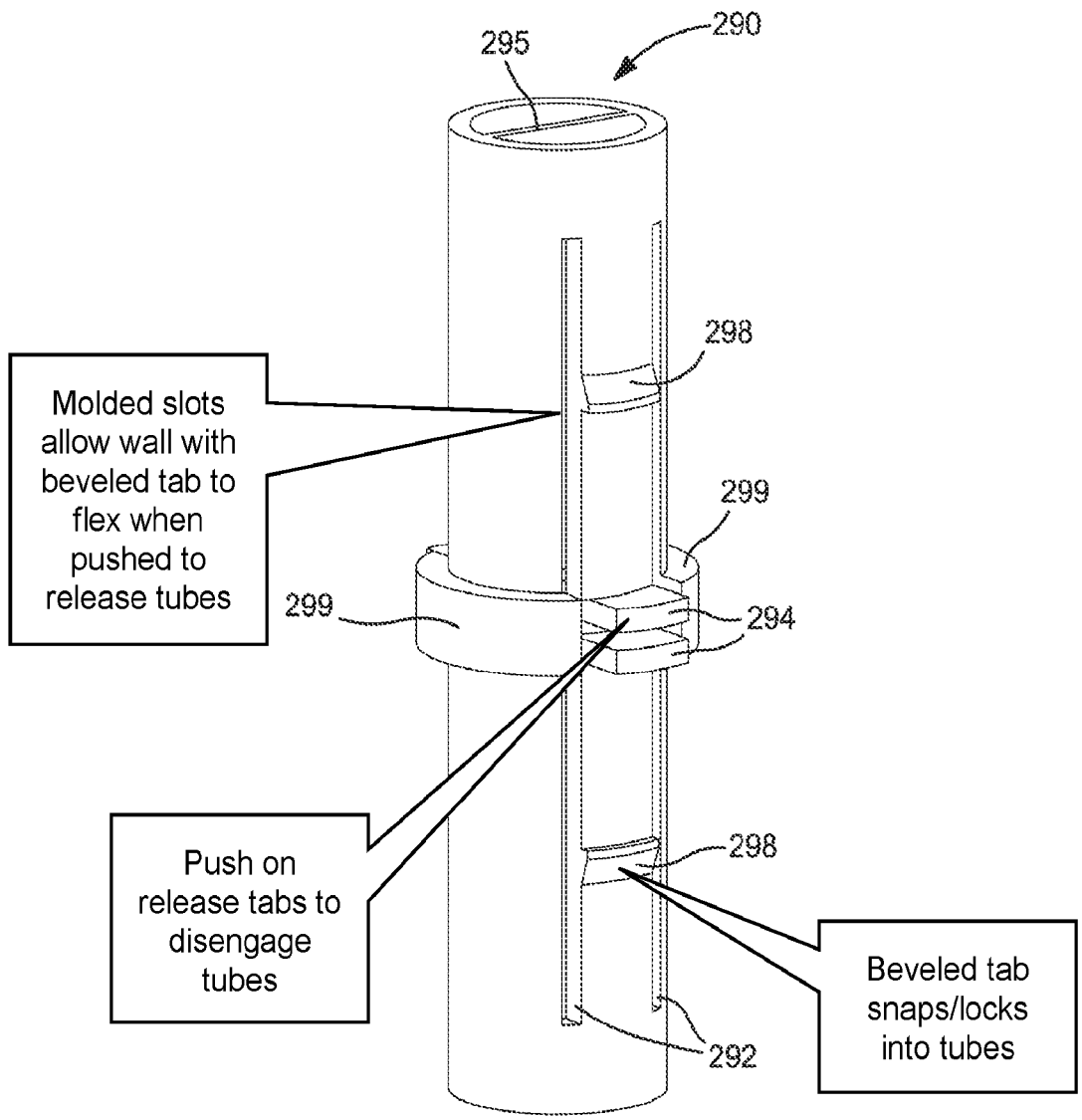
FIG. 14A is an annotated view illustrating features and operation of the connector of FIG. 14.

With reference to FIG. 13, a connector 280 which connects the ball mount 266 of mop 260 to a tube 250 includes a lower base 282 which defines a central opening 284 having a quasi-square form which is complementary to the projecting mounting stud 274. The connector 280 also has a projecting generally cylindrical upper section 286 which is traversed by opposed pairs of slots 287. A pair of opposed depressible retainer tabs 288 project outwardly at intermediate portions of the slots 287. The retainer tabs 288 are similar in form and functions to tabs 238, 278A. The tabs 288 project from a surface which provides for flexure. A tube 250 may be aligned to slide over the connector 280 so that the tabs 288 are received in the slots 252 and the connector 280 is fixed in a one-way connection with the connector 280. The retainer tabs 288 snap into the slots 252 and project outwardly to maintain the connection between the tube 250 and the connector 280. The connector 280 may also have a central panel 289 to provide structural rigidity for the connector 280.

With reference to FIGS. 10, 14, 14A and 16, the connector 290 for the tubes 250 is adapted to connect two tubes 250 in a quasi-end-to-end elongated linear relationship and is longitudinally symmetrical about a medial longitudinal plane. The length of the connector 290, in one embodiment, is approximately 2.1 inches and is preferably less than 2.5 inches. The connector 290 includes longitudinal slots 292 which provide flexure portions adjacent pairs of longitudinally and angularly spaced release tabs 294 which project radially. Two pairs of opposed upper and lower projectable retention pinch tabs 298, similar in form and function with tabs 238, 278A and 288, are employed to selectively and inwardly displace so that either tube 250 may be disconnected from the connector 290. The tabs 294 are individually depressible in the direction of the arrows to allow for inward flexure and displacement (schematically illustrated by line L in FIG. 16) so that the retention tabs 298 may be withdrawn or retracted from the slots 252. A central partition 295 with a medial boss 297 is formed to provide reinforcement at the central portion of the connector 290. A pair of arcuate collar sections 299 provides a stop for ends of the tubes 250.

The release tabs 294 are pushed inwardly so that the tubes 250 can be disengaged and disassembled. The slots 252 allow for the flexure of the tabs 298 so that the tabs 298 snap into the slots 252 and lock into the tubes 250. The required force exerted on tabs 294 to retract one tab 298 is 150 grams. In some embodiments, the tabs 294 are not positioned opposite of one another. It is also possible only a single tab 294 is employed adjacent each longitudinal end.

Figure 15:
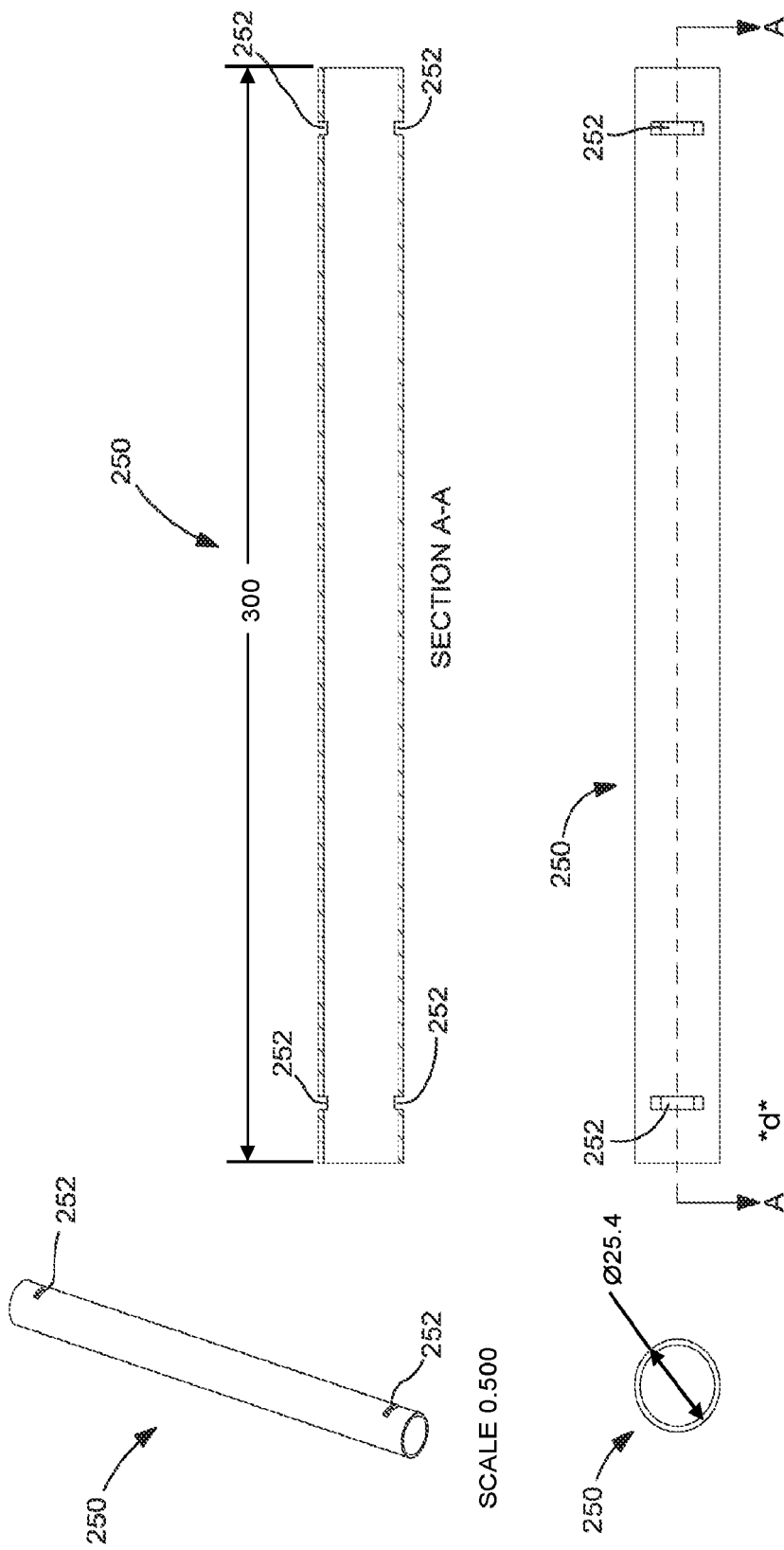
FIG. 15 is an annotated drawing, partly diagrammatic, illustrating a tube which may be employed in the system of FIG. 1.
Figure 16:
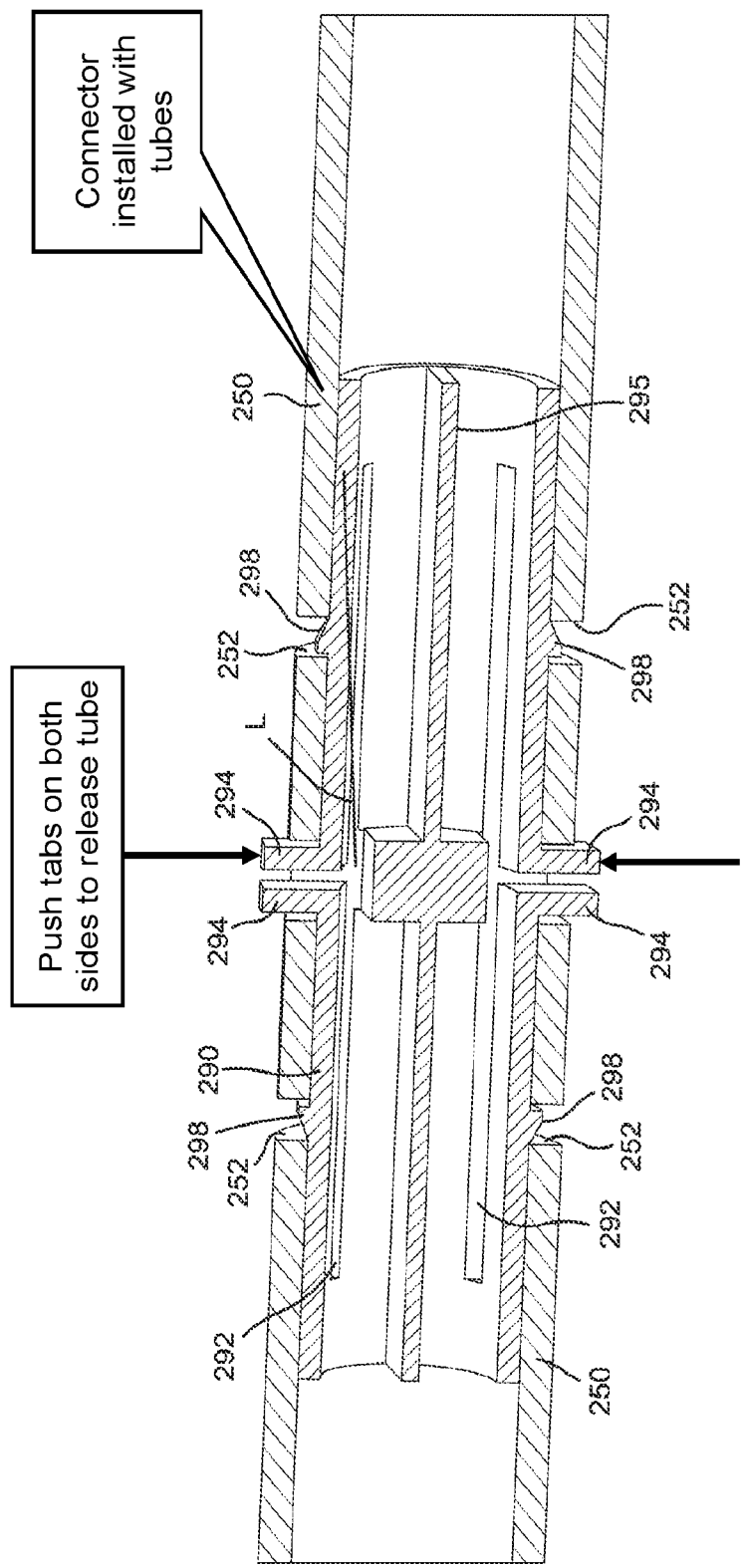
FIG. 16 is an annotated view, partly in section, illustrating the tube connector of FIG. 14 connecting two tubes as illustrated in FIG. 15.

With reference to FIG. 15, one preferred embodiment of a tube 250 may have a length of, for example, 300 mm and a diameter of approximately 25 mm. Two longitudinally spaced pairs of peripheral arcuate slots 252 in the tube 250 are positioned at a uniform distance from the end of the tube 250 which provides sufficient integrity once they are connected to the connectors 290. The tube slots 252 are positioned (preferably within 4 inches from the ends of the tube 250) so that the connectors are not unduly bulky.

Figure 18:
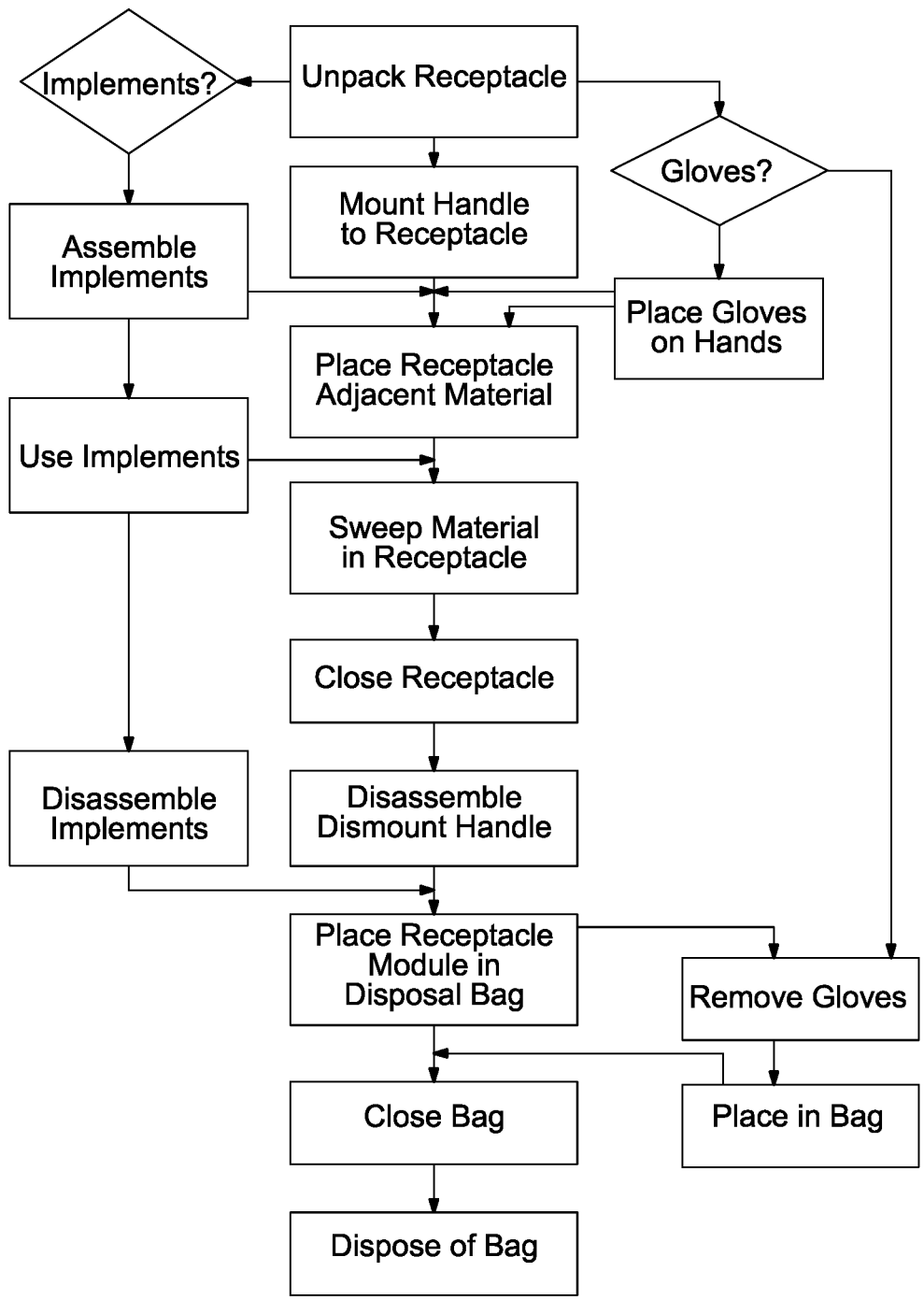
FIG. 18 is a functional block diagram illustrating an embodiment of the system.

As depicted in FIG. 18, one method for the biohazardous material cleanup procedure is concisely described as follows:

Step 1: Place caution signs adjacent to the site of the biohazardous material to prevent foot traffic across spill site.

Step 2: Put on protective devices including eye/face mask, gloves, gown and shoe covers.

Step 3: Pour absorbent powder in and around the biohazardous material.

Step 4: Work absorbent powder into fluids of the biohazardous material with the disposable wiper blade 190 and/or broom 220, 220A.

Step 5: If absorbent powder becomes gummy or if a liquid residue remains, add more absorbent powder and work it into the area until surface is clean and dry.

Step 6: Remove all the used absorbent powder and biohazardous material by using the wiper blade 190 and/or the broom 220, 220A to sweep the absorbent powder into the receptacle 110 and/or dustpan 240 making sure the floor is completely clean and clear of debris. Carefully place the used absorbent powder into a biohazard bag.

Step 7: Disassemble the broom 220, 220A and the dustpan 240 and attach new tubes 250 to the saturated mop 260, 260A.

Step 8: Thoroughly mop the area of the spill with the mop 260, 260A.

Step 9: Disassemble the mop 260, 260A and place in the biohazard bag.

Step 10: Remove all protective clothing including eye/face mask, gloves, gown and/or shoe covers and place into the biohazard bag. Wipe hands with provided antiseptic towelette and also place in the biohazard bag.

Step 11: Close the bag with the twist tie.

Step 12: Dispose of the biohazard bag in accordance with facility waste and disposal policies; including any jurisdictional laws, regulations and/or guidelines governing the disposal of bodily fluids.

Step 13: Thoroughly wash hands with disinfectant soap and water.

Figure 17:
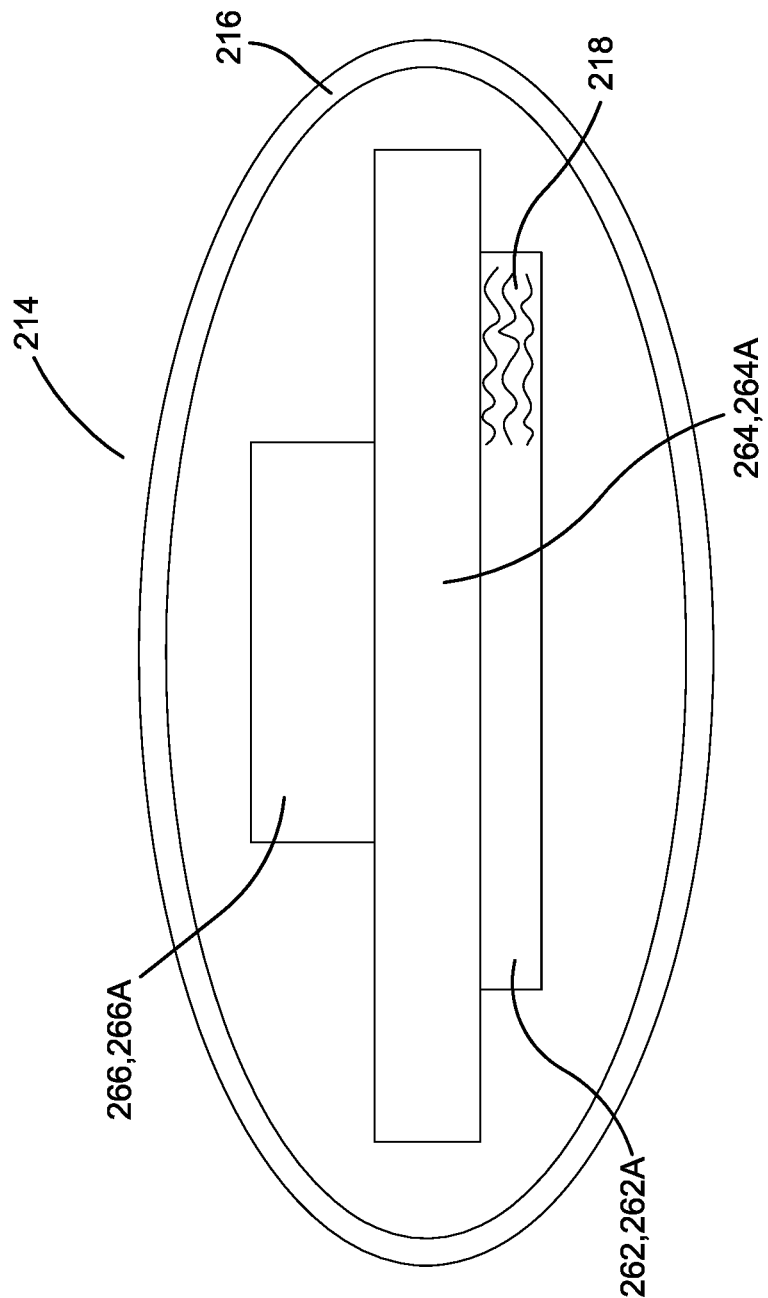
FIG. 17 is a schematic view of the mop of FIG. 11 or 12 prior to assembly.

When the powder is swept up into the receptacle 110, the next procedure is to assemble and employ the mop 180, 260, 260A. With reference to FIG. 17, the mop 180, 260, 260A may be removed from a cover 216. It will be appreciated that the pad 184, 262, 262A of the mop 180, 260, 260A is a pre-saturated with a disinfectant 218 and enclosed in cover 216. The mop 260, 260A is locked into place on the tube 170, 250 as previously described. The locking eliminates spraying and splattering of any contamination in the surrounding environment. The locked mop 180, 260, 260A also ensures that the employees are never closer than three feet from a potential hazard.

The mop 180, 260, 260A also has a high degree of functionality with a flexible living hinge 158, 272A and/or a full swivel capability. The length of the handle 160, 261, 261A for the mop 180, 260, 260A can be increased to a suitable height by easy assembly and disassembly of the tubes 170, 250 or sections of the handle 160, 261, 261A to provide for varying height levels as required. The tube 170, 250 connecting to the mop 180, 260, 260A remains connected to prevent contact with the mop 180, 260, 260A. It will be appreciated that after usage of the mop 180, 260, 260A is completed, the additional tubes 170, 250 may be removed, and all components of the mop 180, 260, 260A may be enclosed in a biohazard bag for disposal.

While embodiments of the disclosed bodily fluid cleanup system 100 has been set forth for purposes of illustration, the foregoing description should not be deemed a limitation of the invention. Accordingly, various modifications, adaptations and alternatives may occur to one skilled in the art without departing from the spirit of the disclosure and the scope of the claimed coverage.

The invention claimed is:

1. A receptacle for cleaning biohazardous material comprising:
    a base having a bottom, two opposed base sides, a rear and an open front having a front edge;
    an integral cover pivotable to said rear comprising a top, two opposed cover sides and gussets connecting the base sides and the cover sides;
    a molded bottom edge insert mounted to said base and forwardly inclined to contact a floor, said bottom edge insert having a rearward retainer lip;
    a molded mounting member attached to said cover having an integrally mounted hinged connector, said molded mounting member closely engageable with said front edge,
    wherein, said receptacle is capable of transitioning between an open position so that material may be swept into said base and a closed position so that the material may be retained for disposal.

2. The receptacle of claim 1, comprising a plurality of anti-skid members mounted to an underside of said bottom of said base.

3. The receptacle of claim 1, wherein said cover defines a pair of opposed apertures and said insert includes a pair of opposed projections and said projections releasably lock into said apertures when the receptacle is in a closed position.

4. The receptacle of claim 1, wherein said molded bottom edge and said molded mounting member are formed from plastic materials.

5. The receptacle of claim 1, wherein said gussets create an over-center configuration which provides a closing and locking force urging said cover to close over said base.

6. The receptacle of claim 1, wherein said bottom edge insert and said mounting member edge are complementarily inclined to engage along an angled interface.

7. The receptacle of claim 1, wherein said base and cover are formed from materials selected from the group consisting of paperboard, corrugated paperboard, cardboard and semi-rigid fibrous materials.

8. The receptacle of claim 1, wherein a bag of disposable modular components for assembling a plurality of modular implements is included within the receptacle in a pre-usage configuration.

9. The receptacle of claim 8, wherein the plurality of modular implements comprises a mop and a wiper blade.

10. The receptacle of claim 9, wherein the wiper blade is comprised of a blade-like component and at least one tube.

11. The receptacle of claim 9, wherein the wiper blade is comprised of a blade-like component and a plurality of tubes, said tubes engaging in a one-way connection with a connector.

12. A modular assembly for cleaning biohazardous material comprising:
a receptacle including a base, an integral cover, a molded bottom edge insert and a molded mounting member, said base having a bottom, two opposed base sides, a rear and an open front having a front edge, said cover capable of pivoting to said rear and comprising a top, two opposed cover sides and gussets connecting the base sides and the cover sides, said bottom edge insert mounted to said base and forwardly inclined to contact a floor, said bottom edge insert having a rearward retainer lip, and said mounting member attached to said cover and engageable with said front edge;
a disposable modular implement configured to move biohazardous material,
wherein, biohazardous material is movable into said base with said implement and said cover is closable over said base to retain the biohazardous material.

13. The modular assembly of claim 12, wherein said receptacle and said disposable modular implement each include a handle assembly.

14. The modular assembly of claim 12, and further comprising a disposable modular mop and a disposable modular broom.

15. A receptacle for cleaning biohazardous material comprising:
a base having a bottom, two opposed base sides, a rear and an open front having a front edge;
an integral cover pivotable to said rear comprising a top, two opposed cover sides and gussets connecting the base sides and the cover sides;
a bottom edge insert mounted to said base and forwardly inclined to contact a floor, said bottom edge insert having a rearward retainer lip;
a molded mounting member attached to said cover having an integrally mounted hinged connector, said molded mounting member closely engageable with said front edge,
wherein, said receptacle is capable of transitioning between an open position so that material may be swept into said base and a closed position so that the material may be retained for disposal.

16. The receptacle of claim 15, comprising a plurality of anti-skid members mounted to an underside of said bottom of said base.

17. The receptacle of claim 15, wherein said cover defines a pair of opposed apertures and said insert includes a pair of opposed projections and said projections releasably lock into said apertures when the receptacle is in a closed position.

18. The receptacle of claim 15, wherein said bottom edge and said molded mounting member are formed from plastic materials, and said base and cover are formed from materials selected from the group consisting of paperboard, corrugated paperboard, cardboard and semi-rigid fibrous material.

19. The receptacle of claim 15, wherein said gussets create an over-center configuration which provides a closing and locking force urging said cover to close over said base.

20. The receptacle of claim 15, wherein said bottom edge insert and said mounting member edge are complementarily inclined to engage along an angled interface.

* * * * *